United States Patent [19]

Ingolia et al.

[11] Patent Number: 5,070,020

[45] Date of Patent: Dec. 3, 1991

[54] RECOMBINANT DNA EXPRESSION VECTORS AND DNA COMPOUNDS THAT ENCODE DEACETOXYCEPHALOSPORIN C SYNTHETASE

[75] Inventors: Thomas D. Ingolia; Steven Kovacevic; James R. Miller, all of Indianapolis; Paul L. Skatrud, Greenwood, all of Ind.

[73] Assignee: Eli Lilly and Company, Indianapolis, Ind.

[21] Appl. No.: 192,273

[22] Filed: May 9, 1988

[51] Int. Cl.[5] .................. C12N 15/63; C12N 15/52; C12N 15/80; C12N 15/76

[52] U.S. Cl. .................. 435/183; 435/252.33; 435/252.35; 435/254; 435/255; 435/172.3; 435/320.1; 536/27

[58] Field of Search .................. 536/27; 435/69.1, 183, 435/172.3, 320, 252.3

[56] References Cited

U.S. PATENT DOCUMENTS 4,510,246 4/1985 Wolfe et al. .................. 435/183

4,536,476 8/1985 Wolfe et al. .................. 435/183

FOREIGN PATENT DOCUMENTS 0233715 8/1987 European Pat. Off. .

OTHER PUBLICATIONS

Jensen et al., Sep. 1983, Antimicrobial Agents and Chemotherapy 24(3):307.

Jensen et al., Feb. 1985, The Journal of Antibiotics XXXVIII(2):263.

Samson et al., 1987, Bio/Technology 5(11).

Primary Examiner—Richard A. Schwartz
Assistant Examiner—S. L. Nolan
Attorney, Agent, or Firm—Amy E. Hamilton; Leroy Whitaker

[57] ABSTRACT

The present invention provides DNA compounds that encode deacetoxycephalosporin C synthetase (DAOCS) activity. The compounds can be used to construct recombinant DNA expression vectors for a wide variety of host cells, including *E. coli, Penicillium, Streptomyces, Aspergillus,* and *Cephalosporium.*

50 Claims, 16 Drawing Sheets

RECOMBINANT DNA EXPRESSION VECTORS AND DNA COMPOUNDS THAT ENCODE DEACETOXYCEPHALOSPORIN C SYNTHETASE

SUMMARY OF THE INVENTION

The present invention comprises a DNA sequence that encodes deacetoxycephalosporin C synthetase activity. Deacetoxycephalosporin C synthetase (DAOCS) catalyzes the reaction in which deacetoxycephalosporin C (DAOC) is formed from penicillin N and is often referred to as expandase. This reaction is a critical step in the biosynthesis of important antibiotics, such as cephalosporins from *Cephalosporium acremonium* and 7α-methoxycephalosporins or cephamycins from *Streptomyces clavuligerus* and *S. lipmanii*.

The DNA compounds of the present invention encode the DAOCS in a single open reading frame. Transcription of this open reading frame, followed by translation of the resulting mRNA, yields a single polypeptide chain that possesses DAOCS activity. The DNA compound that encodes the DAOCS activity was isolated from *Streptomyces clavuligerus* genomic DNA and used to construct recombinant DNA expression vectors. Four types of these expression vectors are especially useful: the first drives high-level expression of the DAOCS activities in *E. coli*; the second in Cephalosporium; the third in Penicillium; and the fourth in Streptomyces.

The *E. coli*-produced DAOCS activity catalyzes the formation of DAOC from penicillin N. Crude cell extracts of these *E. coli* transformants of the invention exhibit DAOCS activity. These *E. coli* expression vectors and transformants provide an efficient means for obtaining large amounts of active DAOCS enzyme. The DAOCS enzyme is useful not only for the production of DAOC and but also for the expansion of penicillins other than penicillin N.

The Cephalosporium vectors of the present invention are useful for purposes of constructing strains for use by the pharmaceutical industry. Cephalosporium is an economically important organism used to produce cephalosporin antibiotics. Transformation of Cephalosporium with the expression vectors of this invention results in higher intracellular levels of DAOCS in the transformants. These transformants can be used to increase the efficiency of, and yield of antibiotic in, industrial fermentation processes. Transformation of *C. acremonium* strains that lack a functional DACS/DAOCS gene with vectors of the invention yields transformants that synthesize DAOC in place of cephalosporin C. DAOC is useful as an intermediate in the preparation of orally absorbed, clinically important antibiotics.

The Penicillium vectors of the present invention are most useful to introduce cephalosporin synthesizing activities into high-level penicillin producing Penicillium strains. The DAOCS activity is useful for conversion of the various penicillins to cephalosporins, either alone or in conjunction with other activities, such as deacetylcephalosporin C synthetase (DACS, which catalyzes the formation of deacetylcephalosporin C from DAOC, a hydroxylation reaction) or epimerase. For example, concomitant expression of isopenicillin N epimerase activity and DAOCS activity in Penicillium leads to production of DAOC, a heretofore unknown metabolite in Penicillium.

The DNA compounds encoding DAOCS are readily modified to construct expression vectors that increase the efficiency and yield of fermentations involving other organisms, such as Paecilomyces and Streptomyces, especially *S. clavuligerus*. Although the DAOCS-encoding DNA of the present invention was isolated from *S. clavuligerus*, this DNA can be used to construct vectors that drive expression of DAOCS in a wide variety of host cells, as illustrated by the *E. coli* expression vectors described above. The construction protocols utilized for the *E. coli*, Cephalosporium, and Penicillium vectors of the invention can be followed to construct analogous vectors for other organisms, merely by substituting, if necessary, the appropriate regulatory elements. Most organisms that produce cephalosporins utilize the common precursor penicillin N, a substrate for DAOCS. The DAOCS-encoding DNA compounds of the present invention can be used to construct expression vectors useful for improving the efficiency and yield of fermentations involving a wide variety of penicillin and cephalosporin antibiotic-producing organisms.

The following section provides a more detailed description of the present invention. For purposes of clarity and as an aid in the understanding of the invention, as disclosed and claimed herein, the following items are defined below.

amdS—an acetamidase gene; also used in the Figures to denote the *Aspergillus nidulans* acetamidase gene.

amdSp—the promoter of the amdS gene.

AmR—the apramycin resistance-conferring gene; also used to denote the apramycin-resistant phenotype.

Antibiotic—a substance produced by a microorganism that, either naturally or with limited modification, will inhibit the growth of or kill another microorganism or eukaryotic cell.

Antibiotic Biosynthetic Gene—a DNA segment that encodes an activity necessary for an enzymatic reaction in the process of converting primary metabolites into antibiotics or converting one antibiotic compound into a different antibiotic compound.

Antibiotic-Producing Organism—any organism, including, but not limited to, Streptomyces, Bacillus, Monospora, Cephalosporium, Paecilomyces, Podospora, Penicillium, and Nocardia, that either produces an antibiotic or contains genes that, if expressed, would produce an antibiotic.

Antibiotic Resistance-Conferring Gene—a DNA segment that encodes an activity that confers resistance to an antibiotic.

ApR—the ampicillin resistance-conferring gene; also used to denote the ampicillin-resistant phenotype.

Bifunctional Cloning Shuttle Vector—a recombinant DNA cloning vector that can replicate and/or integrate into organisms of two different taxa.

bGH—bovine growth hormone or DNA encoding same.

bp—a base pair of double-stranded DNA.

CAT—the chloramphenicol resistance-conferring gene, which encodes an acetyltransferase.

cDACS/DAOCS—the expandase (DAOCS)/hydroxylase (DACS) gene of Cephalosporium acremonium.

cI857—a gene encoding a temperature sensitive repressor of the λpL promoter.

cIPS—isopenicillin N synthetase or isopenicillin N synthetase-encoding DNA from *Cephalosporium acremonium*.

Cloning—the process of incorporating a segment of DNA into a recombinant DNA cloning vector.

Coding sequence—the sequence of DNA in a gene that encodes either the amino acid residue sequence of the protein expressed by the gene or, in the case of rRNA or tRNA genes, the RNA sequence of the rRNA or tRNA expressed by the gene.

Coding strand—the "sense" strand, the single strand of a double-stranded coding sequence that is the complement of the "anti-sense" strand. The anti-sense strand is transcribed by RNA polymerase.

cos—phage λ cohesive end sequences.

Cosmid—a recombinant DNA cloning vector that can replicate in a host cell in the same manner as a plasmid but that can also be packed into phage heads.

DAC—deacetylcephalosporin C, which has the structure depicted below:

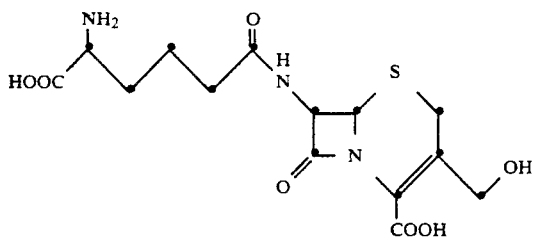

DACS—deacetylcephalosporin C synthetase, the enzymatic activity that catalyzes conversion of DAOC to DAC.

DAOC—deacetoxycephalosporin C, which has the structure depicted below:

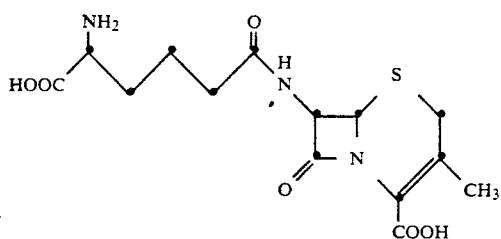

DAOCS—deacetoxycephalosporin C synthetase, the enzymatic activity encoded by the DAOCS gene, which catalyzes conversion of penicillin N to DAOC.

Gene—a segment of DNA that comprises a promoter, translational activating sequence, coding sequence, and 3' regulatory sequences positioned to drive expression of the gene product, either a protein (and thus necessarily an mRNA), tRNA, or rRNA.

Genomic Library—a set of recombinant DNA cloning vectors into which segments of DNA, which substantially represent the entire genome of a particular organism, have been cloned.

hGH—human growth hormone or DNA encoding same.

HmR—the hygromycin resistance-conferring gene; also used to denote the hygromycin-resistant phenotype.

Hybridization—the process of annealing two single-stranded DNA molecules to form a double-stranded DNA molecule that may or may not be completely base-paired.

IPS or IPNS—isopenicillin N synthetase.

Isopenicillin N Synthetase—an enzyme, also known as cyclase, that catalyzes the formation of isopenicillin N from δ-(L-α-aminoadipyl)-L-cysteinyl-D-valine.

KmR—the kanamycin resistance-conferring gene; also used to denote the kanamycin-resistant phenotype.

lacI—the E. coli lacI gene.

lacZα—the promoter and β-galactosidase (lacZ) α-fragment derived from the E. coli lac operon.

lppT—the transcription terminator of the E. coli lpp gene.

lppP—the promoter of the E. coli lpp gene.

M13 ORI—the origin of replication of phage M13.

mel—the tyrosinase gene.

MCS—a multiple-cloning site.

mRNA—messenger ribonucleic acid.

ORI—a plasmid or vector origin of replication, the DNA sequence that serves as an attachment or start site for DNA polymerase.

Pen DNA—DNA from Penicillium chrysogenum.

pIPS—the IPS gene or IPS coding sequence of Penicillium chrysogenum.

pIPSp—the promoter of the IPS gene of Penicillium chrysogenum.

pIPSt—the transcription terminator of the IPS gene of Penicillium chrysogenum.

pL—the leftward promoter from bacteriophage lambda.

Promoter—a DNA sequence that promotes transcription of adjacent DNA.

rbs—ribosome-binding site, a sequence on the 5' end of an mRNA molecule that is encoded by a translational activating sequence and to which ribosomes can bind.

Recombinant DNA Cloning Vector—any autonomously replicating or integrating agent, including, but not limited to, plasmids, comprising a DNA molecule to which one or more additional DNA molecules can be or have been added.

Recombinant DNA Expression Vector—any autonomously replicating or integrating agent, including, but not limited to, plasmids, comprising a promoter and other 5' regulatory sequences positioned to drive expression of a DNA segment that encodes a polypeptide or RNA of research or commercial interest.

Recombinant DNA Vector—any recombinant DNA cloning or expression vector.

Restriction Fragment—any linear DNA molecule generated by the action of one or more enzymes.

rRNA—ribosomal ribonucleic acid.

Sensitive Host Cell—a host cell that cannot grow in the presence of a given antibiotic without a DNA segment that confers resistance thereto.

TcR—the tetracycline resistance-conferring gene; also used to denote the tetracycline-resistant phenotype.

Transcription Terminator—a DNA sequence that acts to block transcription of DNA by RNA polymerase.

Transfectant—a recipient host cell that has undergone transformation by phage DNA or by DNA packaged into a phage particle.

Transformant—a recipient host cell that has undergone transformation.

Transformation—the introduction of DNA into a recipient host cell that changes the genotype and results in a change in the recipient cell.

Translational activating sequence—a 5' regulatory DNA sequence that, when translated into mRNA, promotes translation of mRNA into protein.

tRNA—transfer ribonucleic acid.

trp—the promoter and translational activating sequence of the tryptophan operon of *E. coli*.

BRIEF DESCRIPTION OF THE FIGURES

The restriction site and function maps presented in the accompanying drawings are approximate representations of the recombinant DNA vectors discussed herein. The restriction site information is not exhaustive; therefore, there may be more restriction sites of a given type on the vector than actually shown on the map.

DETAILED DESCRIPTION OF THE INVENTION

Figure 1:
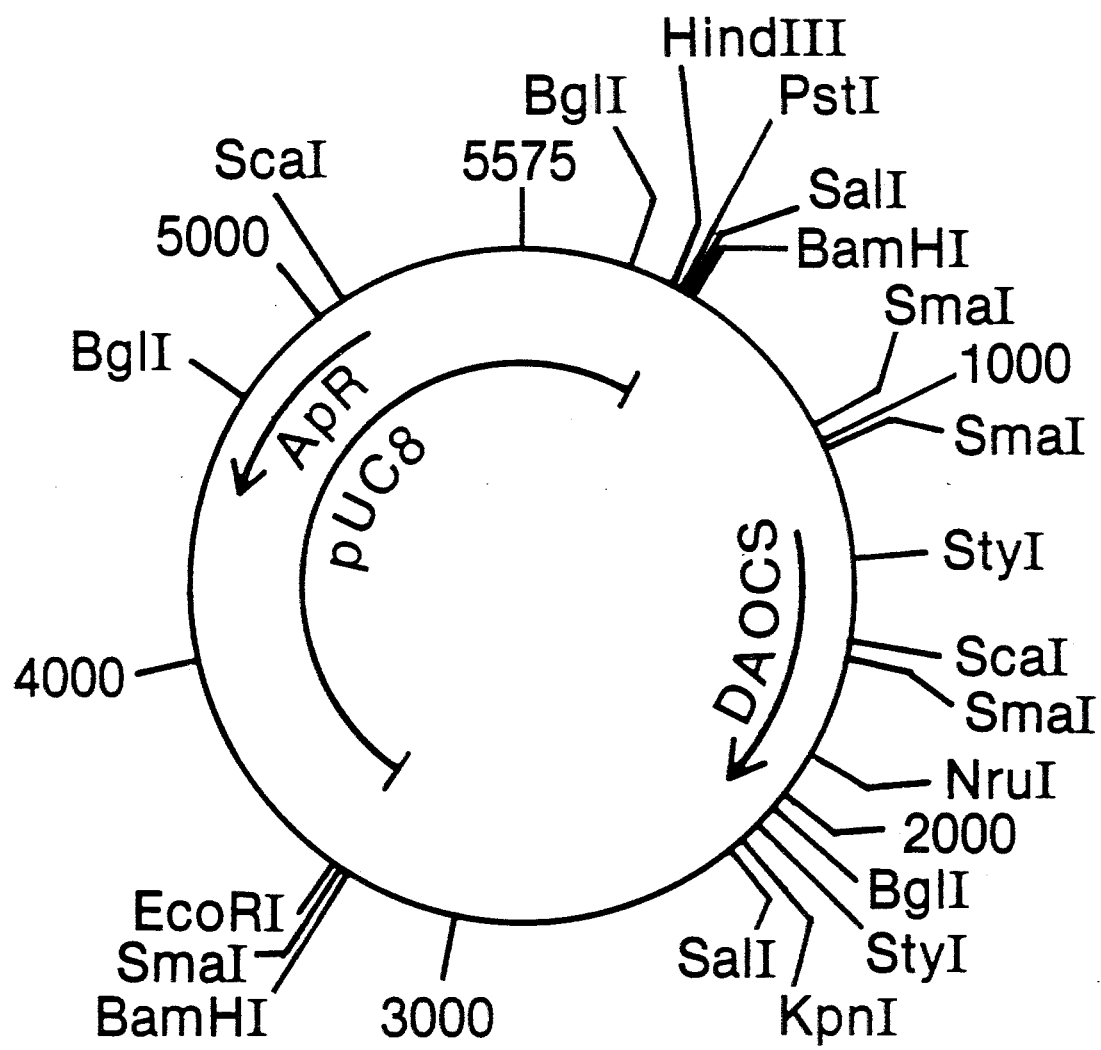
FIG. 1. A restriction site and function map of plasmid pOW380.

The present invention comprises DNA compounds and recombinant DNA cloning and expression vectors that encode the expandase activity of *Streptomyces clavuligerus*. The sequence of the *S. clavuligerus* expandase-encoding DNA is depicted below, together with a portion of the DNA that flanks the 3' and 5' ends of the coding region in the *S. clavuligerus* genome. In the depiction, only the "sense" or coding strand of the double-stranded DNA molecule is shown, and the DNA is depicted from left to right in the 5'→3' orientation. The nucleotide sequence is numbered; the numbers appear above the DNA sequence. Immediately below each line of DNA sequence, the amino acid residue sequence of the expandase encoded by the DNA is listed from left to right in the amino-terminus→carboxy-terminus direction. Each amino acid residue appears below the DNA that encodes it. The amino acid residue sequence is numbered; the numbers appear below the amino acid residue sequence.

```
                           10                              30
         5'-CCC GGG TGC CGC TGG TCA GCG CCA CCG GAT CGA CCC GTA TGG GCC 50                     70                     90
         GCG CCG TGG GCC CCC GGG CCG GTG CTC CGG ATC TCG GCG AAC TTC 110                            130
         TAC ACC ACC GAA GAG GAG ATC GAC CGC CTG GCG GAC GCG CTG GAC 150                           170
         GCG CTG ACG GGC GAG TGA TCC CCC GGG CTC GCG GAC CGC CTC CCC 190                         210
         CGC GCT GTT GAC CAC CCG GTT CAC GGA TTA CGA GAG GAT CAG TGA 230                        250                            270
         GAG TTG ATG GAC ACG ACG GTG CCC ACC TTC AGC CTG GCC GAA CTC
                 Met Asp Thr Thr Val Pro Thr Phe Ser Leu Ala Glu Leu
                  1               5                  10

290                            310
         CAG CAG GGC CTG CAC CAG GAC GAG TTC CGC AGG TGT CTG AGG GAC
         Gln Gln Gly Leu His Gln Asp Glu Phe Arg Arg Cys Leu Arg Asp
          15                  20                  25

330                         350
         AAG GGC CTC TTC TAT CTG ACG GAC TGC GGT CTG ACC GAC ACC GAG
         Lys Gly Leu Phe Tyr Leu Thr Asp Cys Gly Leu Thr Asp Thr Glu
          30                  35                  40

370                          390
         CTG AAG TCG GCC AAG GAC ATC GTC ATC GAC TTC TTC GAG CAC GGC
         Leu Lys Ser Ala Lys Asp Ile Val Ile Asp Phe Phe Glu His Gly
          45                  50                  55

410                          430                         450
         AGC GAG GCG GAG AAG CGC GCC GTC ACC TCG CCC GTC CCC ACC ATG
         Ser Glu Ala Glu Lys Arg Ala Val Thr Ser Pro Val Pro Thr Met
          50                  65                  70
```

-continued

```
              470                              490
CGC CGC GGC TTC ACC GGG CTG GAG TCG GAG AGC ACC GCC CAG ATC
Arg Arg Gly Phe Thr Gly Leu Glu Ser Glu Ser Thr Ala Gln Ile
 75              80                  85

510                              530
ACC AAT ACC GGC AGC TAC TCC GAC TAC TCG ATG TGC TAC TCG ATG
Thr Asn Thr Gly Ser Tyr Ser Asp Tyr Ser Met Cys Tyr Ser Met
 90              95                 100

550                              570
GGC ACC GCG GAC AAC CTC TTC CCG TCC GGT GAC TTC GAG CGG ATC
Gly Thr Ala Asp Asn Leu Phe Pro Ser Gly Asp Phe Glu Arg Ile
105             110                 115

590              610                          630
TGG ACC CAG TAC TTC GAC CGC CAG TAC ACC GCC TCC CGC GCG GTC
Trp Thr Gln Tyr Phe Asp Arg Gln Tyr Thr Ala Ser Arg Ala Val
120             125                 130

650                        670
GCC CGG GAG GTC CTG CGG GCG ACC GGG ACC GAG CCC GAC GGC GGG
Ala Arg Glu Val Leu Arg Ala Thr Gly Thr Glu Pro Asp Gly Gly
135             140                 145

690                              710
GTC GAG GCC TTC CTC GAC TGC GAG CCG CTG CTG CGG TTC CGC TAC
Val Glu Ala Phe Leu Asp Cys Glu Pro Leu Leu Arg Phe Arg Tyr
150             155                 160

730                              750
TTC CCG CAG GTC CCC GAG CAC CGC AGC GCC GAG GAG CAG CCC CTG
Phe Pro Gln Val Pro Glu His Arg Ser Ala Glu Glu Gln Pro Leu
165             170                 175

770                      790                        810
CGG ATG GCG CCG CAC TAC GAC CTG TCG ATG GTC ACC CTC ATC CAG
Arg Met Ala Pro His Tyr Asp Leu Ser Met Val Thr Leu Ile Gln
180             185                 190

830                        850
CAG ACA CCC TGC GCC AAC GGC TTC GTC AGC CTC CAG GCC GAG GTC
Gln Thr Pro Cys Ala Asn Gly Phe Val Ser Leu Gln Ala Glu Val
195             200                 205

870                        890
GGC GGC GCG TTC ACG GAC CTG CCC TAC CGT CCG GAC GCC GTC CTC
Gly Gly Ala Phe Thr Asp Leu Pro Tyr Arg Pro Asp Ala Val Leu
210             215                 220

910                        930
GTC TTC TGC GGC GCC ATC GCG ACC CTG GTG ACC GGC GGC CAG GTC
Val Phe Cys Gly Ala Ile Ala Thr Leu Val Thr Gly Gly Gln Val
225             230                 235

950                      970                        990
AAG GCC CCC CGG CAC CAT GTC GCG GCC CCC CGC AGG GAC CAG ATA
Lys Ala Pro Arg His His Val Ala Ala Pro Arg Arg Asp Gln Ile
240             245                 250

1010                       1030
GCG GGC AGC AGC CGC ACC TCC AGT GTG TTC TTC CTC CGT CCC AAC
Ala Gly Ser Ser Arg Thr Ser Ser Val Phe Phe Leu Arg Pro Asn
255             260                 265

1050                       1070
GCG GAC TTC ACC TTC TCC GTC CCG CTG GCG CGC GAG TGC GGC TTC
Ala Asp Phe Thr Phe Ser Val Pro Leu Ala Arg Glu Cys Gly Phe
270             275                 280

1090                      1110
GAT GTC AGC CTG GAC GGC GAG ACC GCC ACG TTC CAG GAT TGG ATC
Asp Val Ser Leu Asp Gly Glu Thr Ala Thr Phe Gln Asp Trp Ile
285             290                 295

1130                      1150                      1170
GGG GGC AAC TAC GTG AAC ATC CGC CGC ACA TCC AAG GCA TAG AGA
Gly Gly Asn Tyr Val Asn Ile Arg Arg Thr Ser Lys Ala
300             305                 310

1190                       1210
GCA CAC ACC GTC ATG GTC ACA GCA GCA ATC AGT GGT ACC GAC GAG
```

```
                              1230
ATA CGC GCG AGG GCG-3'
``` wherein A is deoxyadenyl, G is deoxyguanyl, C is deoxycytidyl, T is thymidyl, Ala is an alanine residue, Arg is an arginine residue, Asn is an asparagine residue, Asp is an aspartic acid residue, Cys is a cysteine residue, Gln is a glutamine residue, Glu is a glutamic acid residue, Gly is a glycine residue, His is a histidine residue, Ile is an isoleucine residue, Leu is a leucine residue, Lys is a lysine residue, Met is a methionine residue, Phe is a phenylalanine residue, Pro is a proline residue, Ser is a serine residue, Thr is a threonine residue, Trp is a tryptophan residue, Tyr is a tyrosine residue, and Val is a valine residue.

The DNA sequence shown above is ~70% in G and C content and encodes a polypeptide with a calculated molecular weight of 34,519 daltons and an observed molecular weight of about 34,000 daltons. Those skilled in the art will recognize that the DNA sequence depicted above is an important part of the present invention. The above sequence can be conventionally synthesized by the modified phosphotriester method using fully protected deoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765. In addition, an especially preferred method is disclosed in Hsiung et al., 1983, Nucleic Acid Research 11:3227 and Narang et al., 1980, Methods in Enzymology 68:90. In addition to the manual procedures referenced above, the DNA sequence can be synthesized using automated DNA synthesizers, such as the Systec 1450A or ABS (Applied Biosystems, 850 Lincoln Centre Drive, Foster City, Calif. 94404) 380A DNA Synthesizers.

Due to the degenerate nature of the genetic code, which results from there being more than one codon for most of the amino acid residues and translation stop signal, the amino acid residue sequence of DAOCS enzyme depicted above can be encoded by a multitude of different DNA sequences. Because these alternate DNA sequences would encode the same amino acid residue sequence of the present invention, the present invention further comprises these alternate sequences.

The DAOCS encoding DNA compounds of the present invention were isolated from a strain of *Streptomyces clavuligerus*. A genomic library of the total genomic DNA of the *S. clavuligerus* strain was constructed and examined for the presence of sequences homologous to a deoxyribooligonucleotide probe. This probe was constructed in accordance with information obtained about the amino-terminal amino acid sequence of the *S. clavuligerus* DAOCS, with knowledge of the genetic code, and with knowledge of codon usage preferences of Streptomyces. DNA sequencing revealed which vector encoded the *S. clavuligerus* DAOCS.

After the vector that encoded the DAOCS enzyme was identified, an ~3.0 kb BamHI restriction fragment comprising the DAOCS gene was isolated and inserted into commercially available plasmid pUC8 to yield plasmid pOW380, which was then transformed into *E. coli* K12 RR1ΔM15 host cells. The *E. coli* K12 RR1ΔM15/pOW380 transformants have been deposited and made part of the stock culture collection of the Northern Regional Research Laboratories (NRRL), Peoria, Ill. 61604, under the accession number NRRL B-18264. A restriction site and function map of plasmid pOW380 is presented in FIG. 1 of the accompanying drawings.

Plasmid pOW380 serves as useful starting material for the construction of other expression vectors of the invention. These vectors are especially useful in a method for producing DAOCS activity in a recombinant host cell, said method comprising: (1) transforming said host cell with a recombinant DNA expression vector that comprises: (a) a promoter and translational activating sequence; and (b) a DNA sequence that encodes DAOCS activity and is positioned for expression from said promoter; and (2) culturing said host cell transformed in step (1) under conditions that allow for expression of said DAOCS activity.

Plasmid pOW380 can be isolated from *E. coli* K12 RR1ΔM15/pOW380 by the procedure described in Example 1. Plasmid pOW380 serves as useful starting material for vectors of the invention. Plasmid pOW380 contains the intact *Streptomyces clavuligerus* DAOCS gene, which can be isolated, for example, from the plasmid on an ~3.0 kb BamHI restriction fragment. Plasmid pOW380 was used as starting material in the construction of a plasmid, designated pOW382, that drives high-level expression of DAOCS in *E. coli*. To facilitate manipulation of the *S. clavuligerus* DAOCS coding sequence, a restriction enzyme NdeI recognition sequence was created at position −3 to +3 of the *S. clavuligerus* DAOCS DNA coding sequence.

The creation of the NdeI site was done by M13 site-directed mutagenesis technique and involved changing DNA bases in the 5' noncoding portion immediately adjacent to the start codon of the DAOCS gene from GCC to CAT. One skilled in the art will recognize that DNA mutagenesis techniques are commonly used to introduce restriction enzyme recognition sites into DNA sequences and that in this case the encoded amino acid sequence was not changed. The mutagenesis and intermediate constructs are described in greater detailed in Example 2. The resulting plasmid, designated pOW381 and described more fully in Example 2, differs from plasmid pOW380 only in the presence of a restriction enzyme NdeI site. Intermediate plasmid pOW381 was then used to construct expression plasmid pOW382.

Plasmid pOW382 can be constructed by inserting the *Streptomyces clavuligerus* DAOCS coding sequence into plasmid pCZR336, an expression vector that comprises the lambda pL (λpL) promoter and a translation activating sequence, the cI857 temperature sensitive repressor gene, a tetracycline resistance-conferring gene, and DNA sequences encoding vector replication functions. The λpL-derived promoter of plasmid pCZR336 is positioned to drive expression of a first "cistron" encoding a small peptide that precedes the site where the gene of interest can be inserted and expressed under the control of the λpL promoter. At low temperatures of about 30° C., the cI857 protein encoded on plasmid pCZR336 or its derivatives is active and able to repress activity of the λpL promoter, but when the temperature is raised to about 42° C., the cI857 protein is inactivated, and the λpL promoter drives transcription of large amounts of mRNA encoding the gene product of interest. A restriction site and function map of plasmid pCZR336 is presented in FIG. 2 of the accompanying drawings.

Figure 3:
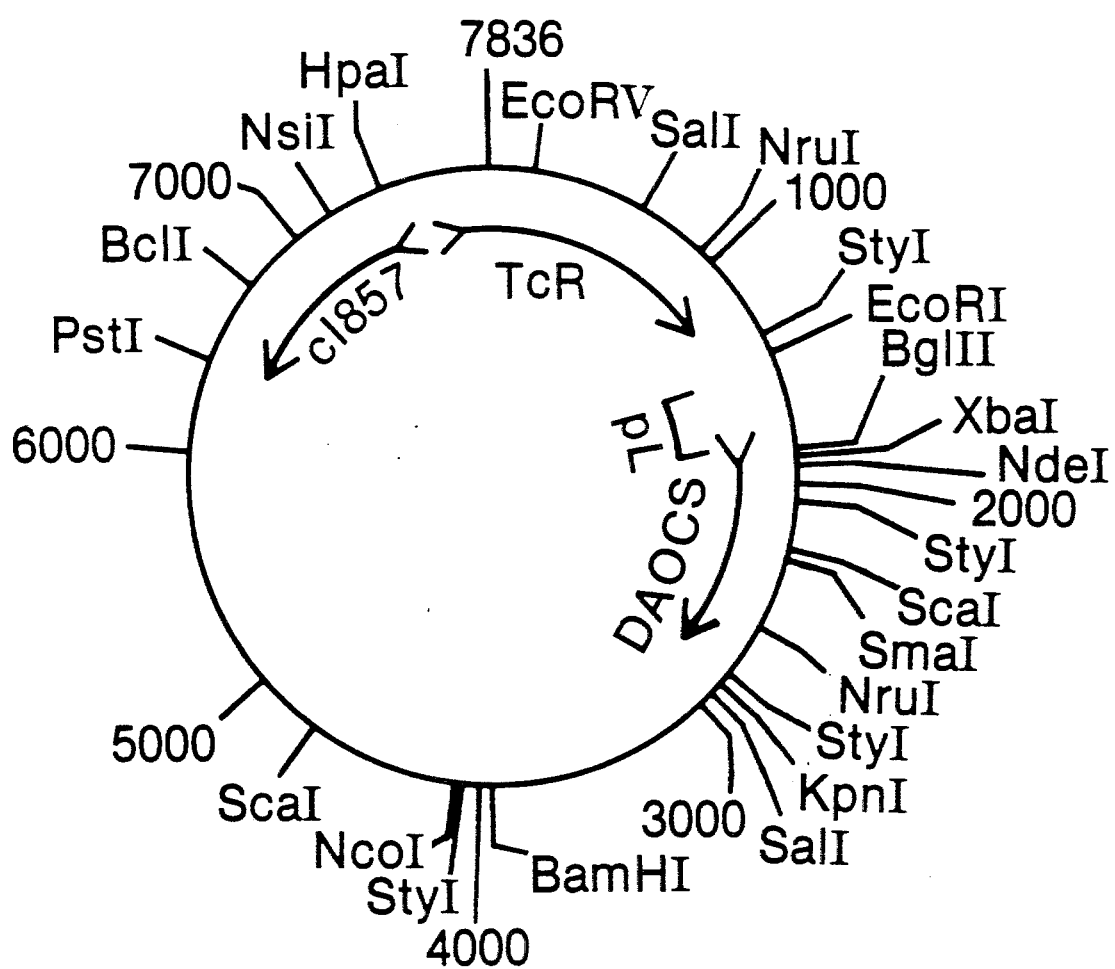
FIG. 3. A restriction site and function map of plasmid pOW382.

Plasmid pOW382 comprises the same first cistron, cI857 gene, λpL promoter, and translational activating sequence as does plasmid pCZR336 but further contains the coding sequence of the DAOCS gene from plasmid pOW381 positioned for expression from the λpL promoter. The ~2.4 kb NdeI-BamHI restriction fragment of plasmid pOW381 comprises the complete coding sequence for DAOCS. Plasmid pOW382 was constructed so that the λpL promoter and the translational activating sequence of plasmid pCZR336 are positioned to drive expression of the DAOCS-encoding DNA. A restriction site and function map of plasmid pOW382 is presented in FIG. 3 of the accompanying drawings. Example 3 describes the construction of plasmid pOW382 in more detail.

At temperatures of about 42° C., $E.$ $coli$ K12 JM109/pOW382 express DAOCS activity at high levels, approaching ~15% of the total cell protein. Crude cell extracts from these $E.$ $coli$ K12 JM109/pOW382 transformants are able to catalyze the conversion of penicillin N into DAOC, whereas cell extracts from non-transformed $E.$ $coli$ K12 JM109 cells cannot catalyze this conversion. The method of assay and results of the assay for the conversion reaction are presented in Example 4.

Many $E.$ $coli$ K12 strains contain an endogenous penicillinase activity, probably encoded by the ampC locus. For this reason it is desirable to effect a partial purification of the DAOCS polypeptide so that optimal DAOCS activity is observed. For these purposes, purification of the enzyme can be used to separate the endogenous $E.$ $coli$ penicillinase activity from the desired DAOCS activity. An alternative to the use of partial purification to overcome the deleterious effects of the penicillinase is to use a strain defective in the production of this activity. One such strain, $E.$ $coli$ K12 A85892, is available from the Northern Regional Research Center under the accession number NRRL B-18096.

Plasmid pOW382 provides an efficient means of producing large amounts of DAOCS in $E.$ $coli.$ Because $E.$ $coli$/pOW382 expresses DAOCS at levels approaching 15% of total cell protein, and because culturing $E.$ $coli$ is less complex than culturing organisms that naturally produce DAOCS, $E.$ $coli$/pOW382 transformants can be used to produce recombinant DAOCS more efficiently and economically than non-recombinant or "natural" DAOCS producers.

DAOCS can be used to produce DAOC from penicillin N in a cell-free system as described in Example 3. DAOC is not only a useful antibiotic, but also can be used as the starting material for the production of such important antibiotics as cephalexin and other cephalosporins (see U.S. Pat. No. 4,307,192). Perhaps the most important use of DAOCS is the use of the enzyme to transform penicillins other than penicillin N into novel cephalosporin derivatives.

Cell-free extracts of penicillin and cephalosporin-producing organisms can be used to synthesize unnatural (not produced in nature) β-lactams. The $E.$ $coli$ expression vectors of the present invention provide an inexpensive and efficient method of obtaining DAOCS, which can be used in vitro to transform penicillins that do not naturally occur in nature to form novel antibiotics or antibiotic core structures.

Plasmid pOW382 is especially preferred for driving expression of DAOCS in $E.$ $coli$ not only because of the high expression levels achieved when using the plasmid but also because of the selectable marker present on the plasmid. Many recombinant DNA vectors encode a β-lactamase, so that cells containing the vector can grow in the presence of certain β-lactam antibiotics, such as ampicillin. However, if one desires to use a cell-free extract containing DAOCS for purposes of constructing β-lactams, one does not want the extract to contain β-lactamase activity. Thus, plasmid pOW382 does not encode a β-lactamase for a selectable marker but rather employs a tetracycline resistance-conferring gene, which encodes a protein that does not react with β-lactams.

The DAOCS expression vectors of the present invention, however, are not limited to a particular selectable marker. Those skilled in the art recognize that many selectable markers are suitable for use on DAOCS expression vectors. Such selectable markers include genes that confer kanamycin resistance, genes that confer chloramphenicol resistance, or other antibiotic resistance-conferring genes.

The search for unnatural penicillins that will serve as substrates for DAOCS can be complemented by a search for mutant DAOCS enzymes that will accept penicillins other than penicillin N as substrate. The present invention provides the starting material for such a search for a mutant DAOCS and comprises DNA compounds derived through mutagenesis of the DAOCS coding sequence. $E.$ $coli$ is a preferred host for mutational cloning experiments, and the $E.$ $coli$ expression vectors of the present invention can be readily mutated by procedures well known in the art, such as, for example, treatment with radiation (X-ray or UV) or chemical mutagens (such as ethylmethanesulfonate, nitrosoguanidine, or methyl methanesulfonate) or site-specific mutagenesis, to obtain mutant enzymes that recognize unnatural penicillins as substrate and catalyze the conversion of those unusual and/or unnatural penicillins to unnatural cephalosporins.

As those skilled in the art will recognize, the present invention allows one to change the codons for the DAOCS gene at will. Given the DNA sequence for the DAOCS gene, only routine procedures are required to generate mutant DAOCS enzymes that vary from the natural DAOCS enzyme at any number of amino-acid residue positions. Such mutant enzymes would be encoded by mutant DAOCS coding sequences, including sequences in which amino-acid codons have been deleted from or inserted into the natural DAOCS coding sequence. Such mutant DAOCS enzymes are within the scope of the present invention, because even if one cannot absolutely predict whether a given mutation will destroy activity of the encoded DAOCS, one need merely express the mutant sequence to ascertain the effect on DAOCS activity.

One particularly useful effect on DAOCS activity is the alteration in substrate specificity that allows penicillin G or penicillin V to serve as substrates for ring-expansion to cephalosporin G or cephalosporin V. These latter antibiotics have a phenylacetic acid or phenoxyacetic acid side-chain in place of the D-alpha-aminoadipoyl side chain of cephalosporin C and are very amenable for processing to 7-aminodeacetoxycephalosporanic acid, an important intermediate in manufacture of orally absorbed, clinically useful cephalosporins.

The present invention is not limited to the particular vectors exemplified herein. Instead, the present invention comprises DNA compounds that encode the DAOCS activity of *Streptomyces clavuligerus*. The DNA compounds of the present invention can be used to construct expression vectors that drive expression of DAOCS activity in any host cell in which the expression vector replicates or integrates and in which the promoter and translational activating sequence used to express the DAOCS activity functions.

Therefore, although the *E. coli* expression vectors exemplified herein utilize a two cistron construction whose transcription is driven by λpL in *E. coli*, the present invention comprises any *E. coli* expression plasmid or vector that drives expression of DAOCS in *E. coli*. Thus, the present invention comprises expression vectors that drive expression of DAOCS and utilize a replicon functional in *E. coli*, such as, for example, a replicon from such plasmids as pBR322, pACYC184, F, ColV-K94, R1, R6-5, or R100. Nor is the present invention solely limited to plasmid vectors, for the present invention also comprises expression vectors that express DAOCS activity and utilize integration or viral replication to provide for replication and maintenance in the host cell.

The present invention is not limited to a particular promoter and translational activating sequence to drive expression of the DAOCS synthetase activity-encoding DNA. The present invention comprises the use of any promoter and translational activating sequence that functions in *E. coli* and is used to express DAOCS in *E. coli*. Many promoter and translational activating sequences functional in *E. coli* are known and are suitable for driving expression of DAOCS activity in *E. coli*. Such transcriptional and translational activating sequences include, but are not limited to, the lpp, lac, trp, tac, λpL, and λpR promoter and translational activating sequences.

In addition to the various *E. coli* transcriptional and translational activating sequences exemplified above, transcriptional and translational activating sequences from other organisms can be ligated to the present DAOC synthetase-encoding DNA compounds to form expression vectors that drive expression of DAOC synthetase activity in host cells in which the activating sequence functions. Although *E. coli* is the host best suited for DAOCS production and subsequent purification for in vitro use, vectors that drive expression of DAOC synthetase activity in host cells other than *E. coli* are also useful, especially for purposes of increasing the cephalosporin antibiotic-producing ability and efficiency of a given organism.

A variety of organisms produce β-lactam antibiotics. The following Table presents a non-comprehensive list of β-lactam antibiotic-producing organisms.

TABLE I

| β-Lactam Antibiotic-Producing Organisms | |
|---|---|
| Organism | Antibiotic |
| Agrobacterium | various β-lactams |
| Arachnomyces | penicillins and |
| minimus | cephalosporins |
| Anixiopsis | penicillins and |
| peruviana | cephalosporins |
| Cephalosporium | penicillins and |
| acremonium | cephalosporins |
| purpurascens | |
| polyaleurum | |
| chrysogenum | |
| curtipes | |
| Chromobacterium | various β-lactams |
| Emericellopsis | penicillins and |

TABLE I-continued

| β-Lactam Antibiotic-Producing Organisms | |
|---|---|
| Organism | Antibiotic |
| terricola | cephalosporins |
| minima | |
| synnematicola | |
| glabra | |
| mirabilis | |
| salmosynnemata | |
| Gluconobacter | various β-lactams |
| Nocardia | |
| lactamadurans | cephamycin C |
| uniformis | nocardicin |
| Paecilomyces | |
| carneus | penicillins and cephalosporins |
| persicinus | |
| Penicillium | various penicillins and |
| chrysogenum | other β-lactams |
| Serratia | various β-lactams |
| Spiroidium | penicillins and |
| fuscum | cephalosporins |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, penicillins, cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxy-cephalosporin C |
| lipmanii | cephamycin, penicillin N, 7-methoxycephalosporin C, A16884, MM 4550, MM 13902 |
| olivaceus | epithienamycin F, MM 4550, an MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

Many of the foregoing β-lactam antibiotic-producing organisms are used in the pharmaceutical industry for purposes of antibiotic production. The antibiotic-producing ability of these organisms can be increased and made more efficient by increasing the intracellular concentration of the antibiotic biosynthetic enzymes during the fermentation. The DAOCS activity-encoding DNA compounds of the present invention can be used to construct expression vectors that, when transformed into the appropriate host cell, increase the intracellular concentration of DAOCS activity of the transformed host cell and thereby increase the antibiotic-producing ability and efficiency of that cell, provided that the host cell produces a β-lactam antibiotic via an intermediate reaction involving DAOCS activity.

A vector that will increase the intracellular concentration of DAOCS activity of a given host cell into which the vector is transformed requires the following elements: 1) a DAOCS activity-encoding DNA compound of the present invention; and 2) a promoter and translational activating sequence that not only functions in the host cell to be transformed, but also is positioned in the correct orientation and position to drive expression of the DAOCS activity-encoding DNA. Of course, stable transformants can only be obtained if the vector replicates, either as an extrachromosomal element or integrated in the genomic DNA, in the host cell. Thus, a preferred vector might contain sequences that specifically direct replication or integration of the vector in the host cell. However, the presence of such specific replication or integration sequences is not absolutely required, as non-specific integration will usually occur when DNA is introduced into a host cell. A DAOCS expression vector could also comprise an antibiotic resistance-conferring gene or some other element that provides a means of selecting for host cells which contain the vector, but such selectable elements may neither be necessary nor desired when the vector integrates into the chromosomal DNA of the host cell.

By providing the coding sequence of the DAOCS gene of Streptomyces clavuligerus, the present invention provides DAOCS expression vectors for any organism susceptible to transformation. The E. coli DAOCS expression vectors described above illustrate the wide variety of expression vectors of the present invention. However, many of the preferred vectors of the invention are designed to drive expression of DAOCS in a β-lactam antibiotic (including penicillins and cephalosporins) producing cell.

Figure 5:
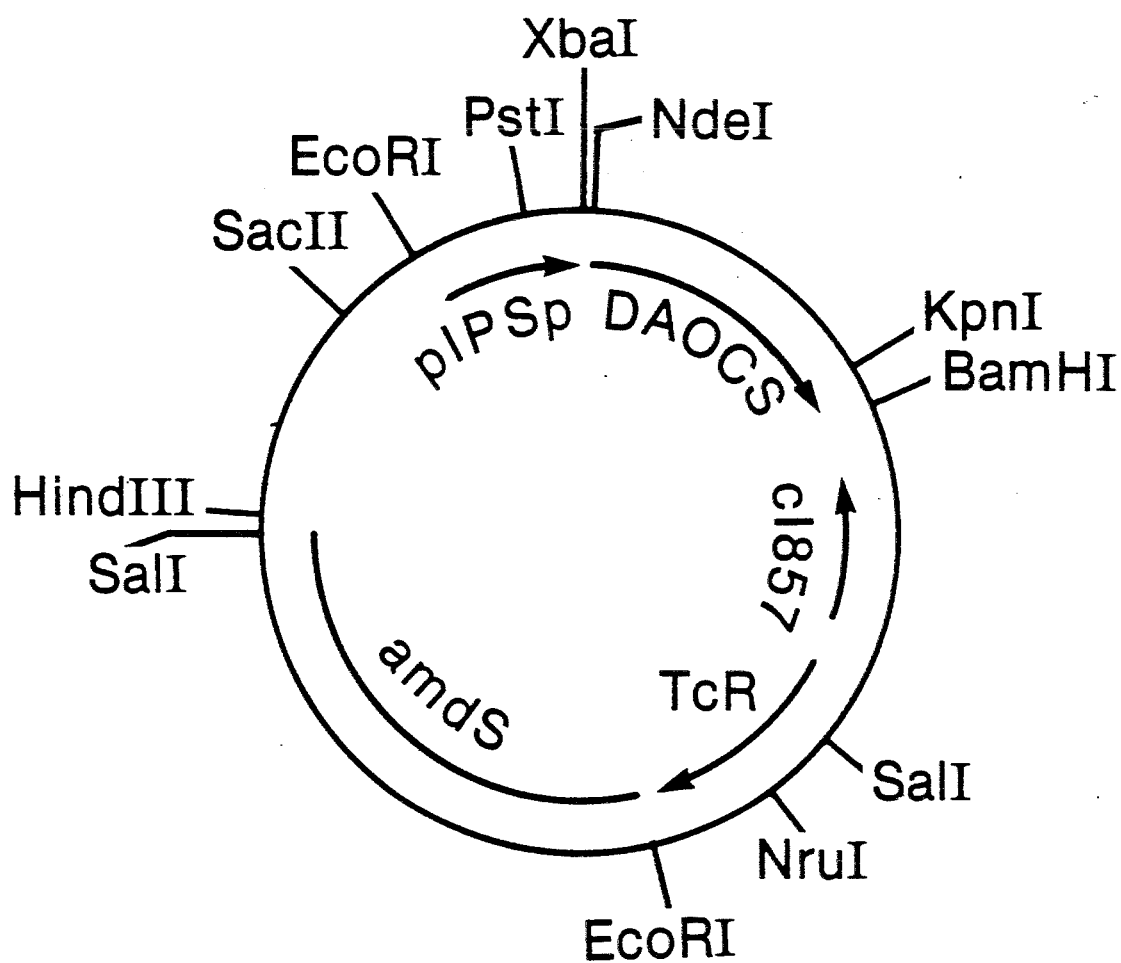
FIG. 5. Restriction site and function map of plasmid pPS65.

The Penicillium vectors of the invention are illustrative of the vectors provided by the present invention that can be used to increase the yield of antibiotic from such a β-lactam antibiotic-producing cell or to alter the antibiotic normally produced by the cell. One such illustrative vector, designated plasmid pPS65, contains the promoter of the Penicillium isopenicillin N synthetase (IPNS) gene positioned to drive expression of the DAOCS coding sequence of the present invention. A restriction site and function map of plasmid pPS65 is provided in FIG. 5 of the accompanying drawings, and the construction protocol for plasmid pPS65 and a variety of useful intermediates is set forth in Example 5.

Another illustrative DAOCS expression vector, designated plasmid pPS67, can be used in Penicillium, Aspergillus, and related host cells. Plasmid pPS67 contains the promoter of the Aspergillus amdS gene, which also functions in Penicillium, positioned to drive expression of the coding sequence of the Streptomyces clavuligerus DAOCS gene. A restriction site and function map of plasmid pPS67 is presented in FIG. 6 of the accompanying drawings. Plasmid pPS67 can be readily modified to contain a selectable marker for use in Penicillium and Aspergillus, as illustrative vectors pPS71 and pPS72, which contain the selectable amdS gene, demonstrate. The construction protocol for plasmids pPS67, pPS71, and pPS72 is set forth in Example 6.

Figure 7:
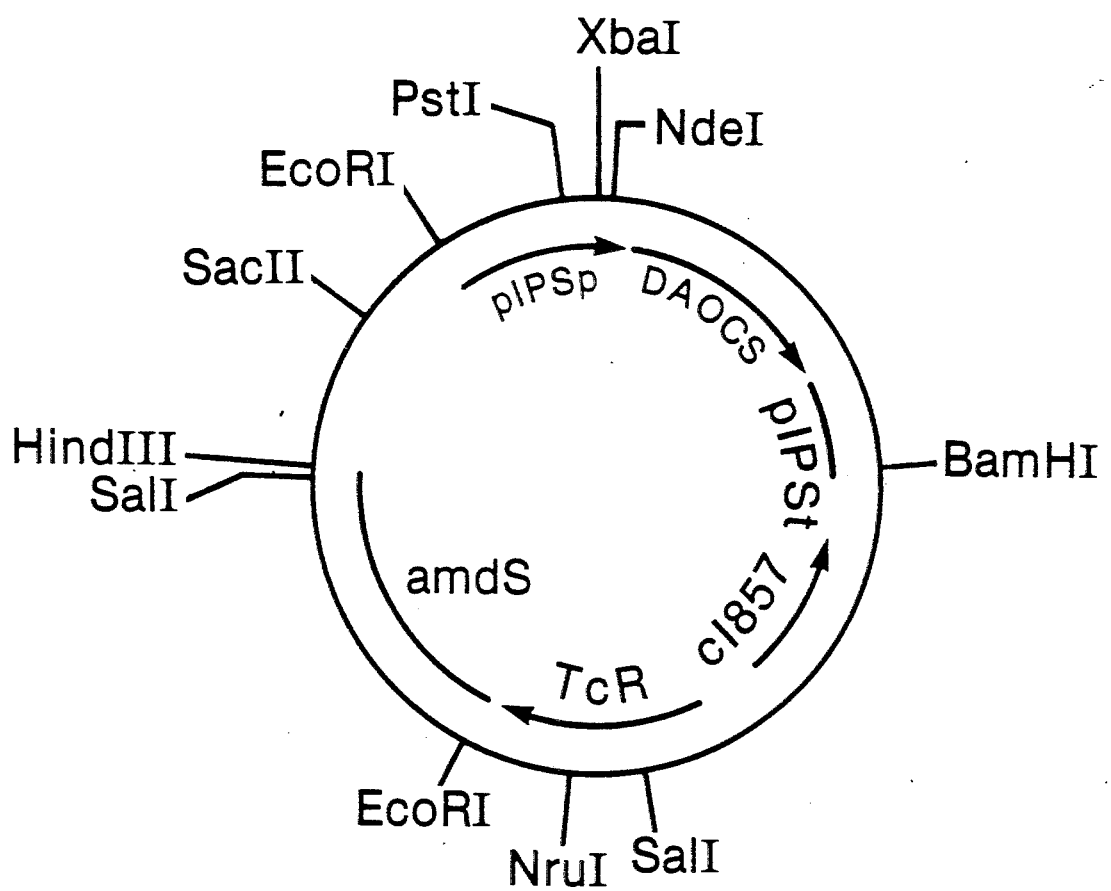
FIG. 7. Restriction site and function map of plasmid pPS69.

Plasmid pPS69 of the present invention contains the promoter of the Penicillium IPNS gene positioned for expression of the DAOCS coding sequence of the invention together with DNA, positioned at the 3' end of the DAOCS coding sequence, that contains the regulatory signals from the 3' noncoding region of the Penicillium IPNS gene. These 3' regulatory signals can be used to increase expression of a recombinant product in a host cell that utilizes the signals. A restriction site and function map of plasmid pPS69 is presented in FIG. 7 of the accompanying drawings. The construction protocol for plasmid pPS69 is set forth in Example 7. A protocol for introducing the illustrative DAOCS expression vectors described above into Penicillium is set forth in Example 8.

The vectors described above and in the following Examples are merely illustrative of the wide variety of DAOCS expression vectors provided by the present invention. Thus, U.S. patent application Ser. No. 07/021,836, filed Mar. 4, 1987, incorporated herein by reference, describes the 5' and 3' regulatory signals of the Cephalosporium acremonium expandase-hydroxylase gene. The signals can be combined with the DAOCS coding sequence of the present invention to yield DAOCS expression vectors of the invention especially suited for use in Cephalosporium. U.S. patent application Ser. No. 06/895,008, filed Aug. 8, 1986, incorporated herein by reference, discloses the transcription and translation activating sequences of the Cephalosporium acremonium IPNS gene, which can be fused to the Streptomyces clavuligerus DAOCS coding sequence of the present invention to create a recombinant DAOCS gene that drives expression (when incorporated into an expression vector and the vector introduced into Cephalosporium) of the S. clavuligerus DAOCS coding sequence in Cephalosporium.

The DAOCS expression vectors of the present invention are useful for increasing the intracellular concentration of DAOCS enzyme in any cell, especially β-lactam antibiotic-producing cells. Plasmid pOW380 comprises the coding sequence of the DAOCS gene of Streptomyces clavuligerus, so plasmid pOW380 can be used to construct vectors for increasing the copy number of the DAOCS gene and thus for increasing intracellular concentration of the enzyme. Because the DAOCS coding sequence of the invention was isolated from a Streptomyces host cell, the DAOCS coding sequence is particularly well-suited for use in expression vectors designed to drive high-level expression of DAOCS in Streptomyces host cells. The literature is replete with techniques for constructing Streptomyces expression vectors and for transforming Streptomyces host cells. See, for instance, Garcia-Dominguez et al., 1987, Applied and Environmental Microbiology 53(6):1376-1381. The DAOCS coding sequence of the invention can be readily incorporated into an expression vector that comprises a Streptomyces promoter and replicon, and a variety of known Streptomyces promoters and replicons are available for such use. Table II is an illustrative, but not comprehensive, listing of Streptomyces plasmids from which Streptomyces replicons can be obtained. Those skilled in the art recognize that, so long as the replicon function is not disrupted, all or part of the plasmids listed in the Table may be used to construct vectors that contain the DAOCS gene of the present invention. The plasmid-containing host and depository accession number are also listed in Table II.

TABLE II

| | Streptomyces Plasmids | |
|---|---|---|
| Plasmid | Host | Accession Number |
| SCP2 | Streptomyces coelicolor A3(2) | NRRL 15042 |
| SCP2* | Streptomyces coelicolor M110 | NRRL 15041 |
| pEL7 | Streptomyces ambofaciens/pEL7 | NRRL 12523 |
| pUC6 | Streptomyces espinosus | NRRL 11439 |
| pUC3 | Streptomyces 3022A | NRRL 11441 |

TABLE II-continued

Streptomyces Plasmids

| Plasmid | Host | Accession Number |
|---|---|---|
| SLP1 | Streptomyces lividans | NCIB[1] 11417 |
| pNM100 | Streptomyces virginiae | NRRL 15156 |
| pEL103 | Streptomyces granuloruber A399 12.13/pEL103 | NRRL 12549 |
| pIJ702 | Streptomyces lividans | ATCC[2] 39155 |

[1]National Collection of Industrial Bacterial (NCIB), Torry Research Station, Post Office Box 31, 135 Abbey Road, Aberdeen AB98DG, Scotland, United Kingdom.
[2]American Type Culture Collection, Rockville, MD 20852.

The *Streptomyces clavuligerus* DAOCS coding sequence of the invention can also be put under the control of transcription and translation activating sequences derived from other strains of Streptomyces, as well as from Penicillium, Cephalosporium, or any other host cell to construct a recombinant DAOCS gene for use in the given organism.

The following Examples are provided to further illustrate and exemplify, but do not limit the scope of, the present invention.

EXAMPLE 1

A. Culture of *E. coli* K12 RR1ΔM15/pOW380

A lyophil of *E. coli* K12 RR1ΔM15/pOW380 can be obtained from the Northern Regional Research Laboratories (NRRL), Peoria, Ill. 61604, under the accession number NRRL B-18264 and used directly as the "culture" in the process described below.

One liter of TY broth (8 g tryptone, 5 g NaCl, and 5 g yeast extract per liter) containing 100 μg/mL ampicillin was inoculated with a culture of *E. coli* K12 RR1ΔM15/pOW380 and incubated with aeration at 37° C. overnight (15–18 hours). The resulting culture was used as a source of plasmid pOW380.

B. Isolation of Plasmid pOW380

The culture prepared in Example 1A was centrifuged at 5200 rpm for 10 minutes at 4° C. to pellet the cells. The resulting supernatant was discarded. The cell pellet was resuspended in 28 mL of a solution of 25% sucrose and 50 mM EDTA. About 1 mL of a solution of 20 mg/mL lysozyme in 50% glycerol and 0.25 M Tris-HCl, pH=8.0, and about 1.5 mL of 0.5 M EDTA, pH=8.0, were added to and mixed with the cell suspension. The resulting mixture was incubated on ice for 15 minutes. Three mL of lysing solution (prepared by mixing 3 mL of 10% Triton-X100; 75 mL of 0.25 M EDTA; pH=8.0; and 7 mL of water) were added to the lysozyme-treated cells with gentle mixing. The resulting solution was incubated on ice for another 15 minutes.

The cellular debris was removed from the solution by centrifugation at 17,000 rpm for about 45 minutes at 4° C. About 28.6 g of CsCl and ~1 mL of a 5 mg/mL ethidium bromide solution were added to the ~30 mL of supernatant. Then, the volume was adjusted to 40 mL with water and the solution decanted into an ultracentrifuge tube. The tube was sealed, and the solution was centrifuged at 49,500 rpm for ~18 hours. The resulting plasmid band, visualized with ultraviolet light, was isolated, extracted with salt-saturated isopropanol to remove the ethidium bromide, and dialysed against three changes of ~20 volumes of TE buffer (10 mM Tris-HCl, pH=7.5, and 1 mM EDTA). The dialysate was collected; then, two volumes of ethanol and 0.05 volumes of 3 M sodium acetate solution were added. The ethanol mixture was cooled to −20° C., and the plasmid DNA was pelleted by centrifugation at 10,000 rpm for 30 minutes at −10° C. The resulting pellet was resuspended in ~1 mL of TE buffer and then extracted with an equal volume of a phenol:chloroform mixture (1:1, v/v). The DNA in the aqueous phase was recovered by the addition of 0.1 volume of 3 M NaOAc and 2 volumes of ethanol, followed by incubation at −20° C. for ~30 minutes and centrifugation at 15,000 rpm for 20 minutes. The resulting DNA pellet was rinsed first with 70% ethanol and then with 100% ethanol and dried.

The ~1.5 mg of plasmid pOW380 DNA obtained by this procedure was suspended in 1.5 mL of 0.1× TE buffer and stored at −20° C. A restriction site and function map of plasmid pOW380 is presented in FIG. 1 of the accompanying drawings.

EXAMPLE 2

Construction of Phage mOW380

Identical plasmid constructs can be achieved employing different methods and sources of gene sequences. Phage mOW380 was constructed by ligating the DAOCS gene-containing ~3 kb BamHI restriction fragment of cosmid pOW379 with BamHI-digested, replicative form (RF) M13 vector. The cosmid pOW379 clone originated from a *Streptomyces clavuligerus* genomic cosmid library and was identified by hybridization using not only the IPNS gene of *S. lipmanii* but also a "guessmer" DNA probe designed on the basis of the amino-terminal amino acid residue sequence of purified *S. clavuligerus* expandase and species codon-usage bias. The desired phage M13 clone can be identified using the "guessmer" probe in a plaque hybridization procedure or by restriction enzyme analysis. Because of the present invention, however, the construction of mOW380 is greatly simplified, primarily because plasmid pOW380 can be used as the source of the *S. clavuligerus* DAOCS gene. The M13-derived phage mOW380 was a useful intermediate in the site-specific mutagenesis carried out to create an NdeI restriction enzyme recognition site at the 5' end of the *S. clavuligerus* expandase coding sequence.

A. Isolation of the ~3 kb BamHI Restriction Fragment from Plasmid pOW380

Approximately 25 μg of the plasmid pOW380 DNA in 25 μl 0.1×TE buffer, as prepared in Example 1B, are added to and mixed with 40 μl of 10× BamHI buffer (1.0 M NaCl; 100 mM Tris-HCl, pH=7.5; and 100 mM MgCl₂), 335 μl of glass-distilled water, and 5 μl (~50 units) of restriction enzyme BamHI. Unless otherwise noted, restriction enzymes were obtained from New England Biolabs, 32 Tozer Road, Beverly, Mass. 01915. Unit definitions herein correspond to the particular manufacturer's unit definitions. The resulting reaction is incubated at 37° C. for 90 minutes. The reaction is then extracted with phenol and chloroform, and the BamHI-digested plasmid pOW380 DNA is precipitated with NaOAc and ethanol and then resuspended in 9 μl of H₂O. About 1 μl loading buffer (25% v/v glycerol, 0.05% w/v bromphenol blue, and 0.05% xylene cyanol) is added to the solution of DNA, which is then electrophoresed on a 1% agarose gel until the desired ~3 kb BamHI restriction fragment is clearly separated from the other digestion products.

The electrophoresed DNA was visualized by staining the gel in a dilute solution (0.5 μg/ml) of ethidium bromide and exposing the stained gel to longwave UV light. After the fragments were located, a small slit was made in the gel in front of the ~3 kb fragment, and a piece of Schleicher and Schuell (Keene, N.H. 03431) DEAE membrane was placed in the slit. Upon further electrophoresis, the DNA non-covalently bound to the DEAE membrane. After the desired fragment was bound to the DEAE membrane, the membrane was removed and rinsed with low salt buffer (100 mM NaCl; 0.1 mM EDTA; and 20 mM Tris-HCl, pH=8). Next, the membrane was placed in a small tube and immersed in high salt buffer (1 M NaCl; 0.1 mM EDTA; and 20 mM Tris-HCl, pH=8) and then incubated at 65° C. for 10 minutes to remove the DNA from the DEAE paper. After the 65° C. incubation, the incubation buffer was collected, and the membrane was rinsed with high salt buffer. The rinse solution was pooled with the incubation buffer before collecting the desired DNA fragments.

The volume of the high salt-DNA solution was adjusted so that the NaCl concentration was 0.25 M, and then three volumes of cold, absolute ethanol were added to the solution. The resulting solution was mixed and placed on ice for 10-20 minutes. The solution was then centrifuged at 15,000 rpm for 15 minutes. After another precipitation to remove residual salt, the DNA pellet was rinsed with 70% ethanol, dried, resuspended in 20 μl of TE buffer, and constituted the desired restriction fragment. About 0.6 μg of the ~3 kb fragment was obtained.

B. Preparation of BamHI-Digested Vector M13mp19 RF DNA and Construction of Phage mOW380

About 2.5 μg of M13mp19 RF DNA (available from New England Biolabs (NEB)) were digested in 100 μl of BamHI buffer with 1 μl (~20 units) of restriction enzyme BamHI for 90 minutes at 37° C. The reaction mixture was extracted with phenol:chloroform and the DNA, in the aqueous phase, concentrated by ethanol precipitation. The DNA pellet was resuspended in 20 μl of 0.1× TE buffer and constituted ~2 μg of the desired BamHI-digested M13mp19 vector. The vector DNA obtained was stored at −20° C.

Two μl of the ~3 kb BamHI restriction fragment of plasmid pOW380 and 1 μl of BamHI-digested vector M13mp19 are ligated in a 20 μl reaction containing the DNA fragments, 2 μl of 10× ligase buffer (0.5 M Tris-HCl, pH 7.5, and 100 mM MgCl₂), 2 μl of 5 mM ATP, 1 μl of 6 μg/μl BSA, 12 μl of glass-distilled water, and 1 μl (1 Weiss unit) of T4 DNA ligase (NEB). The reaction is incubated ~18 hours at 15° C. The ligated DNA constitutes the desired phage mOW380 along with other ligation products.

Competent *E. coli* K12 JM109 ("Epicurean Coli ᵀᴹ") were purchased from Stratagene (3770 Tansy Street, San Diego, Calif. 92121) and transformed with a ligation reaction mixture constituting phage mOW380 in substantial accordance with the manufacturer's directions, except that the DNA was in a volume of 20 μl and no dilution into medium or expression time was necessary. Post-transformation, the cells were distributed in ~1, 10, 20, 40 and 50 μl samples to 13×100 mm sterile glass tubes containing 0.25 mL/tube *E. coli* K12 JM109 in logarithmic growth phase. To these tubes were added 3 mL of top agar (L broth with 0.8% agar kept molten at 45° C.). The cell-top agar mixture was then plated on L-agar plates containing 40 μg/mL 5-bromo-4-chloro-3-indolyl-β-D-galactoside (X-gal) and 0.1 M isopropylthio-β-galactoside (IPTG), and the plates were incubated at 37° C. overnight. (For more detailed descriptions and explanations of M13 procedures, see *M13 Cloning/Dideoxy Sequencing Instruction Manual*, Bethesda Research Laboratories (BRL), Life Technologies, Inc., Gaithersburg, Md. 20877.) Transformants are identified by insertional inactivation of β-galactosidase activity (colorless plaque phenotype) and restriction enzyme analysis of replicative form (RF) DNA. For screening purposes, clear plaques are plugged from the plate overlay with a Pasteur pipette into 3 mL per plaque of early logarithmic growth phase *E. coli* K12 JM109. Cultures are incubated from 6 to 18 hours at 37° C. with aeration.

Following this incubation, 1.5 mL of each culture are pelleted in separate 1.5 mL Eppendorf tubes. The supernatants are decanted into fresh tubes and stored at 4° C. to serve as a source of phage inoculum. Replicative form DNA is prepared from the cell pellets in substantial accordance with the teaching of the alkaline plasmid preparation procedure of Birnboim and Doly, 1979, *Nuc. Acid Res.* 7(6): 1513–1523, with the following exceptions. The procedure is scaled up such that 1.5× volumes of Solutions I, II, and III are used, and the cleared lysate is extracted once with an equal volume of CHCl₃. The DNA is then precipitated by the addition of 0.4 volumes of isopropanol and incubation at room temperature for 20 minutes. The DNA is collected by centrifugation and then precipitated with ethanol out of 0.3 M NaOAc. The analysis of the restriction pattern of the RF DNA is facilitated by the existence of an assymetric ScaI restriction enzyme recognition site that is not only diagnostic for the presence of the desired insert but also can be used to orient the insert sequence relative to the multiple-cloning site (MCS) of the M13 vector. By this method, *E. coli* K12 JMI09/mOW380 cells were identified; these cells were then used as a source of phage mOW380 for the site-specific mutagenesis, as described below.

C. Preparation of Single-Stranded Phage mOW380 DNA and Site-Specific Mutagenesis to Construct Phage mOW381

A 10 mL culture of early logarithmic growth phase *E. coli* K12 JM109 was inoculated with ~200 μl of phage stock (prepared in Example 2B) and incubated ~18 hours at 37° C. with aeration. The culture was centrifuged and the resulting supernatant transferred to a new tube and recentrifuged. The supernatant was again decanted to a fresh tube. One mL of a solution of 25% polyethylene glycol (molecular weight≈3,350) in 3 M NaCl was added to the supernatant, which was then incubated for 15 minutes at room temperature. The resulting mixture was centrifuged for 30 minutes at 10,000 rpm. The pellet obtained by the centrifugation contained the single-stranded phage mOW380 and was resuspended in 400 μl of TE buffer. The solution was extracted first with CHCl₃ and then with TE-saturated phenol. The phenol was allowed to stay in contact with the aqueous phase for 15 minutes. The solution was then extracted twice with a mixture of TE-saturated phenol:CHCl₃ (1:1, v/v), and twice with CHCl₃ alone. The DNA was then precipitated out of 0.3 M NaOAc, collected by centrifugation, and the resulting pellet resuspended in 100 μl of 0.1× TE buffer. This solution constituted ~5 μg of single-stranded phage mOW380 DNA.

D. Mutagenesis

The single-stranded DNA fragments used in the mutagenesis (and subsequent hybridizations to detect desired phages) were synthesized on an automated DNA synthesizer, with the exception of the M13 universal primer (a 15-mer), which was purchased from BRL. The mutagenesis fragments were designated as follows: (1) STNDE-A, a single-stranded DNA 41 nucleotides in length that is homologous to the DAOCS coding sequence in phage mOW380 except for three bases, the mismatch (underlined) of which will create a restriction enzyme NdeI recognition sequence at about position 1 of the DAOCS coding sequence, with the DNA sequence:

NdeI
5'-GTGGGCACCGTCGTGTCCATATGCTCTCACTGATCCTCTCG-3'

(2) STNDE-B, a single-stranded DNA 17 nucleotides in length that is merely a subfragment of STNDE-A, with the DNA sequence:

NdeI
5'-TGTCCATATGCTCTCAC-3'

The 5' ends of about 100 pmols of STNDE-A were phosphorylated (kinased) in a reaction mixture containing single-stranded DNA at a concentration of 1 pmol/μl, 10 μl of 10× ligase buffer, 1000 pmols adenosine triphosphate (ATP), 10 μl of 0.1 M DTT, 65 μl of glass-distilled water, and 1 μl (10 Richardson units) of T4 polynucleotide kinase (Boehringer-Mannheim Biochemicals, (BMB) 7941 Castleway Drive, P.O. Box 50816, Indianapolis, Ind. 46250). The reaction mixture was incubated at 37° C. for 30 minutes, at which time an additional 1 μl of enzyme was added. The reaction mixture was then incubated for another 30 minutes at 37° C. and then quenched by incubation at 68° C. for 5 minutes. The 5' ends of about 40 pmols of M13 universal primer were kinased in an analogous 40 μl of reaction mixture containing the same amount of enzyme.

The single-stranded phage mOW380 DNA was mutagenized in substantial accordance with the teaching of Adelman et al., 1983, DNA 2(3): 183–193 as described below. The annealing reaction was carried out by adding ~500 nanograms (in 15 μl of 0.1× TE buffer) of single-stranded phage mOW380 DNA to 8 μl of 10× annealing buffer (100 mM Tris-HCl, pH=7.5; 1 mM EDTA; and 500 mM NaCl), 4 μl (4 pmols) of kinased STNDE-A, 4 μl (4 pmols) of kinased M13 universal sequencing primer, and 50 μl of water, incubating the mixture at 80° C. for 2 minutes, then at 55° C. for 5 minutes, and finally at room temperature for 5 minutes.

The extension reaction was carried out by adding 120 μl of the following mixture to the solution of annealed DNA: 20 μl 10× Klenow-ligase buffer (100 mM Tris-HCl, pH=7.5; 1 mM EDTA; and 500 mM NaCl), 20 μl of 0.1 M DTT; 20 μl of a solution 6.25 mM in each of dGTP, dATP, TTP, and dCTP; 20 μl of 5 mM ATP; 120 μl of water; 1 μl T4 DNA ligase (100-500 units, NEB), and 2.5 μl (12.5 units) of Klenow enzyme (BMB). The extension reaction mixture was incubated at room temperature for 1 hour, then at 37° C. for 4 hours, and finally at 14° C. for ~18 hours.

The extension reaction mixture was extracted once with $CHCl_3$ and the DNA precipitated with ethanol and NaOAc and collected by centrifugation. The DNA pellet was resuspended in 400 μl 1× S1 buffer (0.3 M NaCl and 3 mM ZnOAc). Half the DNA solution was held in reserve at −20° C.; half was aliquoted to five 1.5 mL tubes. To four of these tubes was added 1 μl of S1 nuclease (BMB) that had been diluted to 200 30-minute units per μl. The reactions were incubated at room temperature for 5, 10, 15, and 20 minutes, respectively. The reactions were stopped by first adding 5–10 μg of tRNA to the reaction mixture to serve as carrier, then extracting with a TE-saturated phenol-$CHCl_3$ mixture (1:1, v/v). The sample that was not treated with S1 (the negative control) was also extracted. The DNA in the aqueous phase was concentrated by ethanol precipitation and collected by centrifugation. The DNA pellets were each resuspended in 20 μl water.

Ten μl of each of the resulting S1-treated DNA solutions were used to transform *E. coli* K12 JM109 in substantial accordance with the procedure described in Example 2B, except that the plates did not contain either X-Gal or IPTG. Desired mutants were identified by hybridization of radiolabelled oligonucleotide STNDE-B with phage DNA blotted onto nitrocellulose filters as described below.

After plaque formation, the plates were incubated at 4° C. for ~1 hour to harden the top agar. Nitrocellulose filters were placed on top of the lawn of each of two plates, containing ~50–200 plaques, from each of the negative control, the 10 minute S1-treated series, and the 20 minute S1-treated series. Contact between the filter and the surface of the lawn was maintained for ~1 minute, at which time the nitrocellulose filter was treated, by using saturated 3 MMChr filter papers (Whatman LabSales, Inc., P.O. Box 1359, Hillsboro, Oreg. 97123-1359), with 0.1 N NaOH-1.5 M NaCl for ~5 minutes, then 0.5 M Tris-HCl(pH=7.0)-3 M NaCl for ~5 minutes. The nitrocellulose filters were air-dried and then baked in vacuo at 80° C. for 30 minutes.

The nitrocellulose filters were prehybridized for ~5 minutes at room temperature in a solution of 6× SSC (20× SSC is 3 M NaCl and 0.3 M Na citrate), 10× Denhardt's solution (0.2 g of polyvinylpyrollidone), 0.2 g of bovine serum albumin, and 0.2 g of Ficoll per 100 mL of water), 0.1% NaPPi, 0.1% SDS, and 10 μg/mL of denatured *E. coli* chromosomal DNA. The filters were then hybridized in a solution of 6× SSC, 10× Denhardt's solution, 0.1% NaPPi, and 1 pmol/5 mL of $^{32}$P-STNDE-B. The $^{32}$P-STNDE-B was prepared by phosphorylating the 5' ends of 100 pmols of STNDE-B in substantial accordance with the procedure described earlier in this example, except that ~70 pmol of γ-$^{32}$P-ATP (New England Nuclear (NEN), 549 Albany Street, Boston, Mass., 02118, Catalog #NEG-002A) were used instead of non-radioactive ATP. After hybridization, the filters were rinsed twice for 5 minutes per wash in excess 6× SSC at room temperature, then at 52° C. in excess 6× SSC for 20 minutes per wash. The filters were air-dried and autoradiographed for 2 hours at −70° C. with a Quanta III ® intensifying screen (DuPont, Instrument Products, Biomedical Division, Newtown, Conn. 06470). Desired mutants, those containing sequences complementary to the sequence of STNDE-B, exposed the film due to binding of the radiolabelled oligomer by the phage DNA bound to the filter. The identity of a correct mutant, designated phage mOW381, was confirmed by restriction analysis of its RF DNA, which was prepared in substantial accordance with the procedure described in Example 2B.

E. Final Construction of Plasmid pOW381

Although the RF DNA of phage mOW381 contains the DAOCS coding sequence on the NdeI-BamHI restriction fragment utilized in the construction of the E. coli expression plasmid pOW382, it is sometimes difficult to accumulate the RF of mOW381 in sufficient quantity for fragment isolation. To facilitate the construction of the E. coli expression plasmid pOW382, the intermediate plasmid pOW381 was constructed.

Replicative form DNA from phage mOW381-infected E. coli K12 JM109 was isolated in substantial accordance with the procedure described in Example 2B. About 10 μg of the RF DNA of phage mOW381 DNA were digested with restriction enzyme BamHI (~10 units) in a reaction containing the DNA in 1× BamHI buffer. After incubation for ~90 minutes at 37° C., the reaction mixture was subjected to agarose gel electrophoresis, and the ~3 kb BamHI fragment was isolated in substantial accordance with Example 2A.

BamHI-digested plasmid pUC8 DNA (plasmid pUC8 DNA is available from BRL) was prepared in substantial accordance with the procedure described in Example 2B. Five μl (~1μg) of the ~3 kb BamHI fragment DNA isolated from phage mOW381 and 1 μl (~100 ng) of BamHI-digested plasmid pUC8 DNA were ligated in substantial accordance with the procedure described in Example 2B. The ligated DNA constituted the desired plasmid pOW381 along with other ligation products. Plasmid pOW381 has a restriction site map identical to that of plasmid pOW380, except for the presence of an additional NdeI restriction enzyme recognition sequence located at about the first codon of the DAOCS coding sequence.

The ligation reaction constituting the desired plasmid pOW381 was transformed into competent E. coli K12 RR1ΔM15 (NRRL B-15440). Aliquots of the transformation mixture were plated on L-agar plates containing ampicillin (100 μg/mL), X-gal (40 μg/mL), and IPTG (0.1 M). The plates were incubated at 37° C. for ~18 hours. Ampicillin-resistant transformants with a white colony color (due to insertional inactivation of the α-fragment of β-galactosidase encoded in plasmid pUC8) were further screened by restriction enzyme analysis of their plasmid DNA to identify the desired plasmid pOW381 transformants. Plasmid DNA was prepared from 3 mL cultures in substantial accordance with the Birnboim and Doly procedure described above for preparing RF DNA from phage M13-infected E. coli K12 JM109 cell pellets. Plasmid pOW381 DNA from one transformant was prepared in substantial accordance with the procedure described in Example 1 for use in subsequent constructions.

EXAMPLE 3

Construction of Plasmid pOW382

Plasmid pOW382 can be constructed by ligating together the ~2.4 kb NdeI-BamHI restriction fragment from plasmid pOW381 that contains the Streptomyces clavuligerus expandase (DAOCS) coding sequence and an ~5.8 kb NdeI-BamHI restriction fragment from plasmid pCZR336. The ~5.8 kb NdeI-BamHI fragment from pCZR336 contains DNA sequences coding for the λpL promoter, a translation activating sequence, the cI857 repressor, a plasmid origin of replication, and a tetracycline resistance-conferring gene. Plasmid pCZR366 also contains a coding sequence for human growth hormone. The DNA sequences contained in the ~5.8 kb NdeI-BamHI fragment of plasmid pCZR336 can be constructed as described in Part A of this Example. A restriction site and function map of plasmid pCZR336 is presented in FIG. 2 of the accompanying drawings.

A. Construction of the ~5.8 kb NdeI-BamHI Restriction Fragment of Plasmid pCZR336

Figure 4:
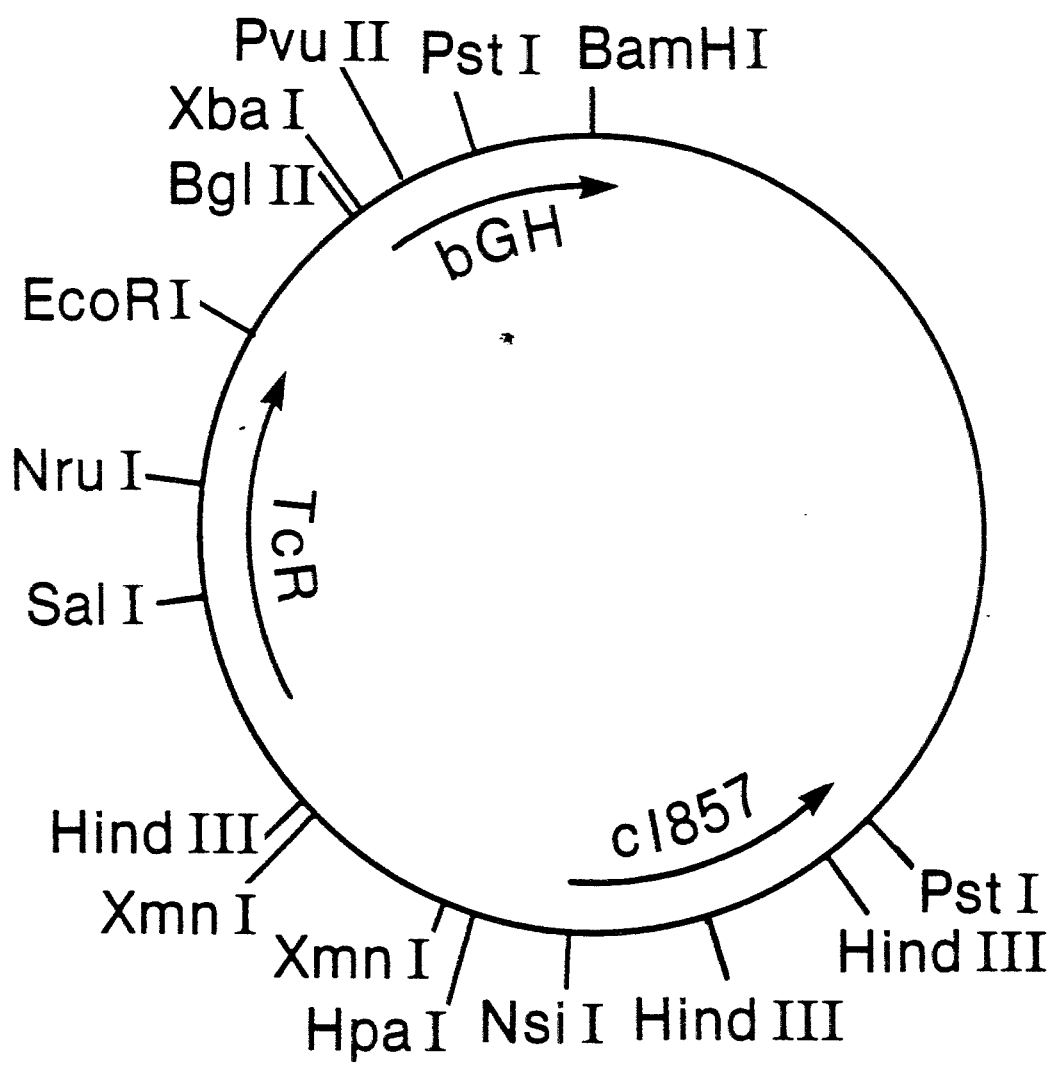
FIG. 4. Restriction site and function map of plasmid pCZR111.

Most of the DNA in the ~5.8 kb NdeI-BamI restriction fragment of plasmid pCZR336 can be isolated from plasmid pCZR111 on an ~5.75 kb XbaI-BamHI restriction fragment. A restriction site and function map of plasmid pCZR111 is presented in FIG. 4 of the accompanying drawings. Plasmid pCZR111 can be obtained from E. coli K12 RV308/pCZR111, available from the NRRL under accession number NRRL B-18249. Plasmid pCZR111 confers resistance to 10 μg/ml tetracycline and lacks a ClaI restriction site.

Figure 2:
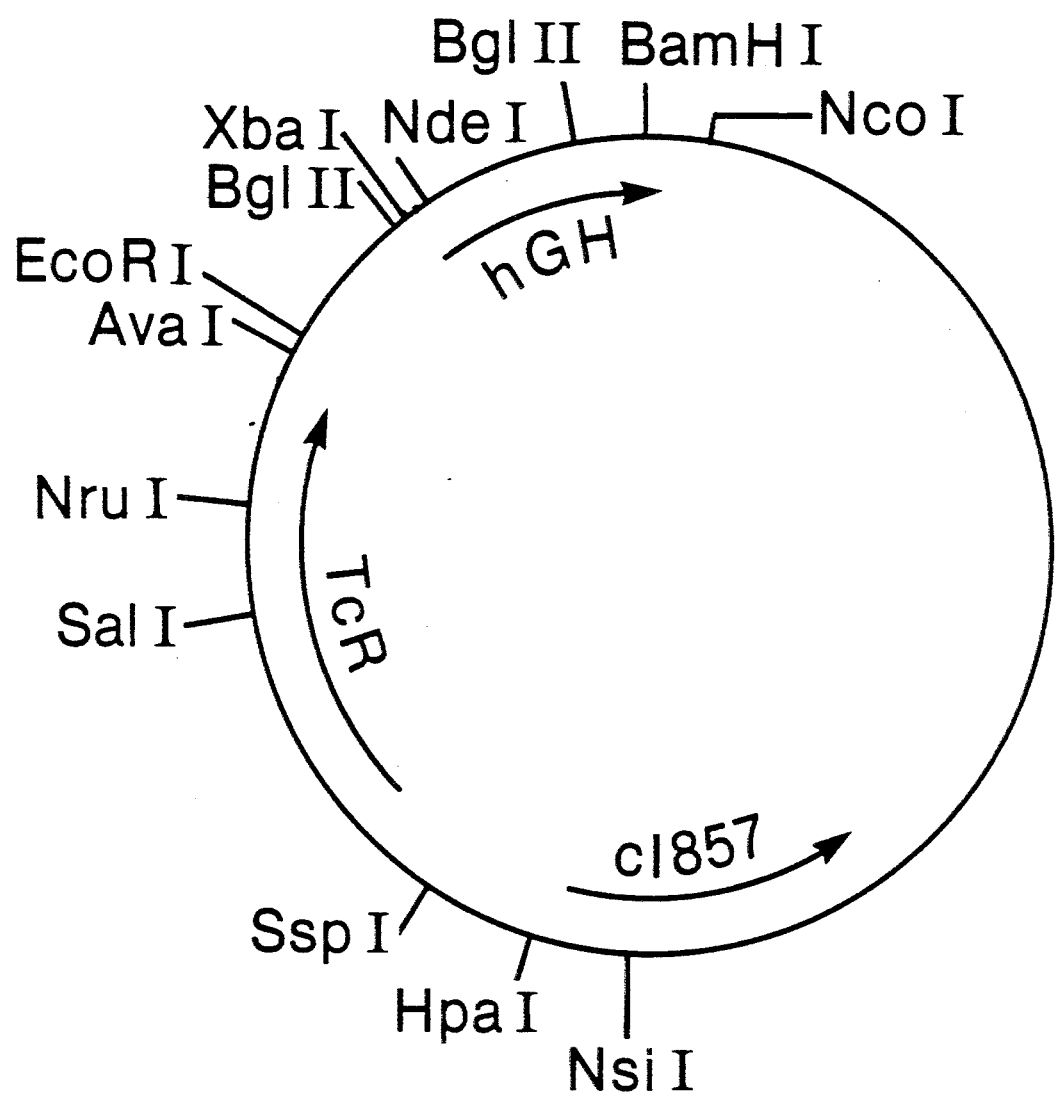
FIG. 2. A restriction site and function map of plasmid pCZR336.

Plasmid pCZR111 is also digested with XbaI and BamHI enzymes, and the large XbaI-BamHI fragment is purified from agarose. This XbaI-BamHI restriction fragment of plasmid pCZR111 is ligated together with a double stranded XbaI-NdeI restriction fragment synthesized by the phosphotriester method to yield the ~5.8 kb NdeI-BamHI restriction fragment of plasmid pCZR336 (FIG. 2). The double stranded DNA fragment has the following sequence:

```
5'-CTAGAGGGTATTAATAATGTATATTGATTTTAATAAGGAGGAATAATCA-3'
   ||||||||||||||||||||||||||||||||||||||||||||||||
3'-    TCCCATAATTATTACATATAACTAAAATTATTCCTCCTTATTAGTAT-5'
```

B. Isolation of ~2.4 kb NdeI-BamHII fragment of Plasmid pOW381

Approximately 25 μg (in 25 μl of 0.1× TE buffer) of plasmid pOW381 DNA were added to and mixed with 4 μl of 10× NdeI buffer (100 mM Tris-HCl, pH 7.8; 70 mM MgCl₂; and 1.5 M NaCl) 6 μl of H₂O, 3 μl of restriction enzyme NdeI, and 3 μl of restriction enzyme BamHI. The resulting reaction mixture is incubated at 37° C. for 2 hours and subsequently subjected to agarose gel electrophoresis. The ~2.4 kb NdeI-BamHI fragment is isolated from the agarose gel and prepared for ligation.

C. Final Construction of Plasmid pOW382 and E. coli K12 JM109/pOW382

About 1 μl (~0.5 μg) of the ~5.8 kb NdeI-BamHI-restriction fragment of plasmid pCZR336 DNA and 4 μl (~0.1 μg) of the isolated ~2.4 kb NdeI-BamHI restriction fragment from pOW381 were ligated in substantial accordance with the procedure described in Example 2. The ligated DNA constitutes the desired plasmid pOW382. A restriction site and function map of plasmid pOW382 is presented in FIG. 3 of the accompanying drawings. The ligation reaction was transformed into competent *E. coli* K12 JM109 cells (Stratagene) in substantial accordance with the manufacturer's directions. The transformation mix was plated onto TY agar plates containing tetracycline (10 μg/mL) and the plates incubated at 25°–30° C. to prevent transcription from the lambda pL promoter. Desired transformants were identified by their tetracycline-resistant phenotype and by restriction enzyme analysis of their plasmid DNA.

EXAMPLE 4

Assay of *E. coli*-produced DAOCS Activity

A. Culture of *E. coli* K12 JM109/pOW382 for Expression of DAOCS Activity

An *E. coli* K12 JM109/pOW382 transformant was grown at 30° C. overnight in 500 ml of L broth (containing 10 μg/ml of tetracycline) in a gyrotory incubator (250 rpm). The cells were diluted 100 fold by adding 10 ml of the overnight culture to 990 ml of fresh medium containing 10 μg/ml tetracycline in a 2.8 L flask and incubated a further hour at 30° C. under the same growth conditions. The temperature of the gyrotory incubator shaker was then raised to 42° C. and incubation continued for an additional 6.5 hours. The cI857 temperature-sensitive repressor of the lambda pL promoter, positioned to drive expression of the DAOCS coding sequence on plasmid pOW382, is inactivated at 42° C., so at 42° C. expression of DAOCS occurs in the host cells. After induction, the cells were harvested by centrifugation and used as a preferred source of *E. coli*-produced DAOCS activity.

B. Demonstration of Expandase (DAOCS) Activity in the *E. coli* K12 JM109/pOW382 Cells Grown at 42° C.

After induction at 42° C. for 6 hours, 250 ml of the *E. coli* culture were harvested by centrifugation and the cell pellet washed in 30 ml of Solution A (15 mM Tris-HCl, pH 7.5, 10% ethanol, 10% glycerol, and 10 mM DTT) plus 1 M KCl. The cells were subsequently washed once in 30 ml of Solution A without KCl and then resuspended in 7 ml of solution A plus 10 mM ascorbic acid. The cells were disrupted by sonication at a temperature of 4° C. or below by three, 30-second bursts at full power. During sonication, multiple additions of phenylmethylsulfonyl fluoride (PMSF) were made until the final concentration was 2 mM. DNAse and magnesium sulfate were added to achieve concentrations of 1 μg/mL and 2 mM, respectively. The sonicated suspension was centrifuged at 40,000× g for 30 minutes. The supernatant provided a crude extract of the DAOCS enzyme.

DAOCS activity was determined using an HPLC-based assay. The expandase-catalyzed reaction is conducted for 15 minutes at 30° C. with 0.28 mM penicillin N, 0.60 mM α-ketoglutarate (α-KG), 0.06 mM ferrous sulfate, 0.67 mM ascorbate, 1.00 mM dithiothreitol, 0.05 mM ATP, and 0.0003–0.003 units of the enzyme in 1 ml of 50 mM Tris.HCl, pH=7.5.

The enzymatic reaction was interrupted by the addition of 1 ml of ethyl alcohol. The precipitate was separated by centrifugation at 4,000× g for 5 minutes. The supernatant containing the enzyme reaction products was assayed by HPLC as follows. The expandase activity was determined by monitoring formation of DAOC from penicillin N.

Samples (20 to 100 μl) of the supernatant solutions were assayed for DAOC by HPLC using external standards. The assays were reproducible with 2% deviations for duplicate analyses of the expandase-catalyzed reaction. The results of the assay are summarized below.

| Enzyme Source | Expandase and Hydroxylase Activities from Various Sources | |
|---|---|---|
| | Specific Activity (U/mg protein) | |
| | Expandase | Hydroxylase |
| *S. clavuligerus* Crude Extract | 0.004 | 0.00023 |
| Recombinant *E. coli* | | |
| Crude Extract | 0.009 | 0 |
| Granular Preparation | 0.052[a] | 0 |

[a]The recovery of the expandase activity was not optimized.

EXAMPLE 5

Construction of Plasmid pPS65

Figure 8:
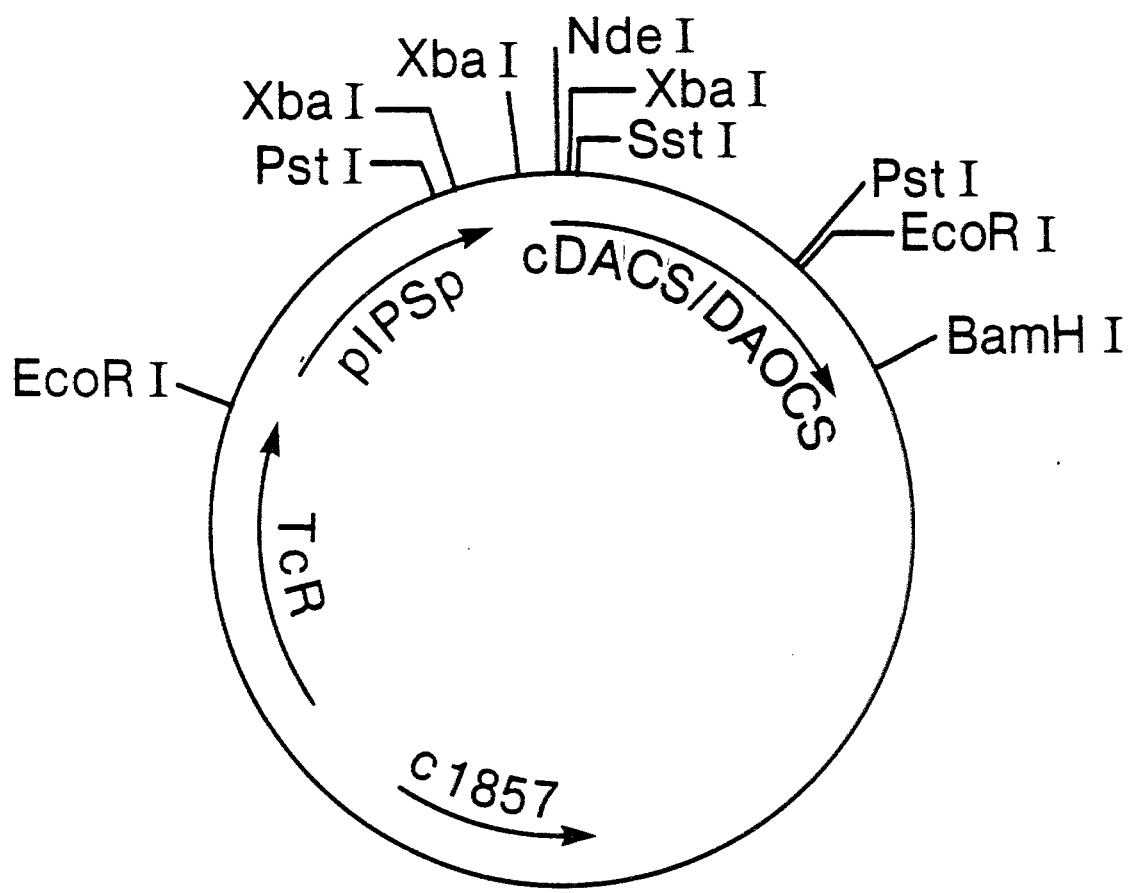
FIG. 8. Restriction site and function map of plasmid pPS60.

This example sets forth a construction protocol for plasmid pPS65, a DAOCS expression vector of the invention that contains the promoter of the Penicillium IPNS gene positioned to drive expression of the DAOCS coding sequence of the invention. The promoter of the Penicillium IPNS gene can be isolated from plasmid pPS60, an expression vector disclosed in Examples 1 through 13 of U.S. patent application Ser. No. 07/021,836, filed Mar. 4, 1987, incorporated herein by reference. A restriction site and function map of plasmid pPS60 is presented in FIG. 8 of the accompanying drawings.

A. Construction of Intermediate Plasmids pPS63 and pPS64

Plasmid pPS60 was digested with restriction enzymes NdeI and BamHI, and the larger of the two resulting NdeI-BamHI restriction fragments was isolated from an agarose gel and prepared for ligation. In a similar fashion, plasmid pOW382 (Example 3, above) was digested with restriction enzymes NdeI and BamHI, and the smaller, DAOCS-encoding, of the two resulting NdeI-BamHI restriction fragments was isolated from an agarose gel and prepared for ligation.

Figure 9:
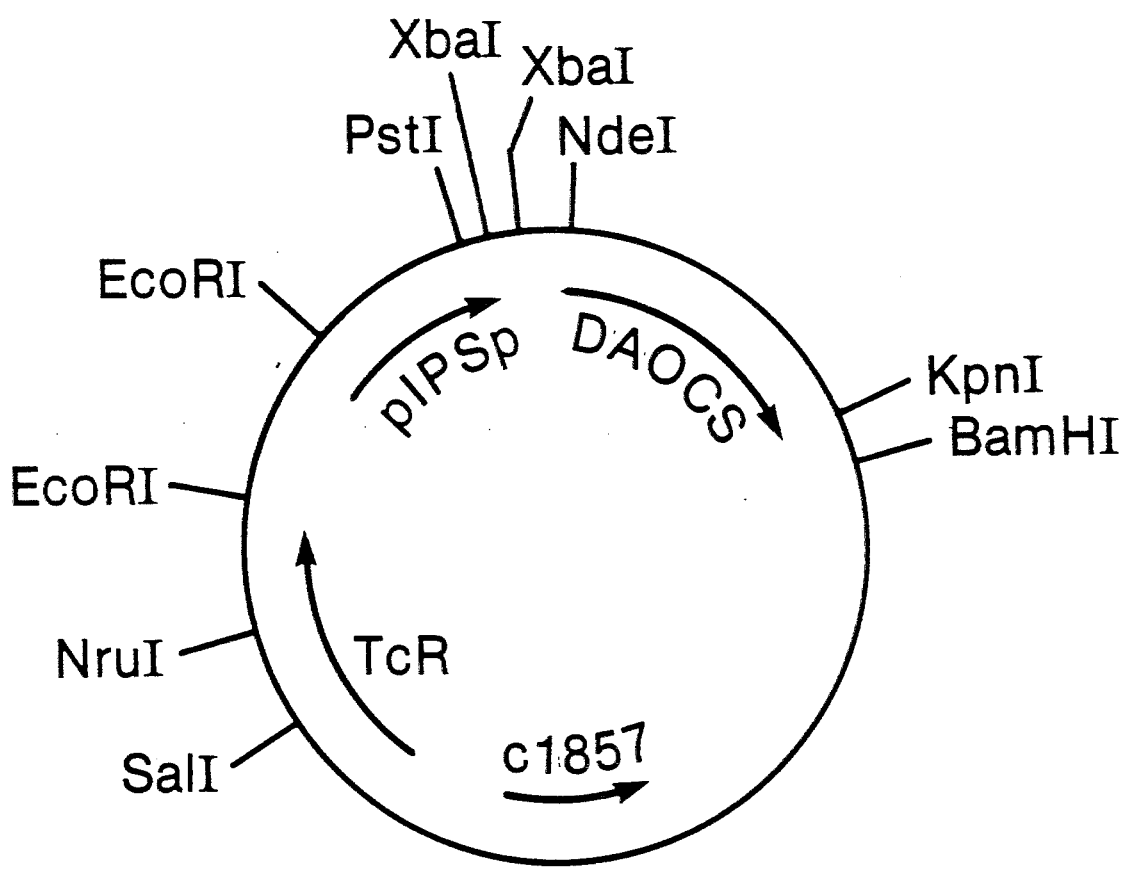
FIG. 9. Restriction site and function map of plasmid pPS63.

The isolated NdeI-BamHI restriction fragment of plasmid pPS60 was then ligated to the DAOCS-encoding NdeI-BamHI restriction fragment of plasmid pOW382 to yield plasmid pPS63. A restriction site and function map of plasmid pPS63 is presented in FIG. 9 of the accompanying drawings. Although plasmid pPS63 contains the promoter of the Penicillium IPNS gene positioned to drive expression of the DAOCS coding sequence, the spacing between the 3' end of the promoter and 5' end of the DAOCS coding sequence is not optimal.

To achieve a more optimal spacing, plasmid pPS63 can be digested with restriction enzymes XbaI and NdeI and the resulting NdeI-Xba-digested plasmid pPS63 DNA mixed with a linker shown below and ligated. This linker has the structure:

```
5'-CTAGACAC-3'
    | | | |
    3'-TGTGAT-5'
```

Figure 10:
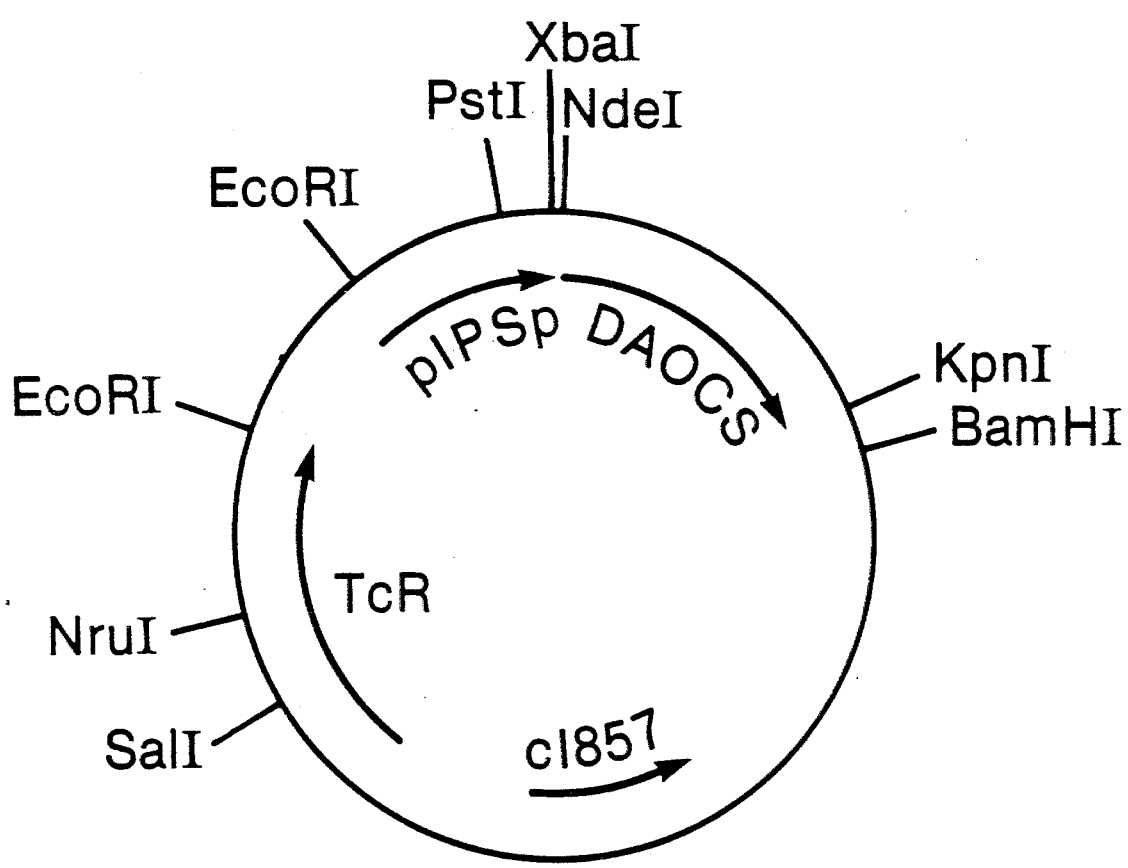
FIG. 10. Restriction site and function map of plasmid pPS64.

The ligated DNA contains plasmids in which the small XbaI-XbaI and XbaI-NdeI restriction fragments located between the 3' end of the Penicillium promoter and 5' end of the DAOCS coding sequence of plasmid pPS63 are replaced with the linker sequence depicted above. One such plasmid was identified by restriction enzyme analysis and DNA sequencing and designated plasmid pPS64. DNA sequencing revealed that more than one linker has been incorporated into the plasmid, so XbaI digestion of the plasmid and religation was used to remove the additional linkers. A restriction site and function map of plasmid pPS64 is presented in FIG. 10 of the accompanying drawings.

B. Addition of the amdS Gene to Plasmid pPS64 to yield Plasmid pPS65

Plasmid pPS64 can be used to drive expression of DAOCS activity in Penicillium host cells. Plasmid pPS64 does not contain, however, a selectable marker, but as is illustrated below, can be readily modified to incorporate such a marker. The amdS gene of *Aspergillus nidulans* is a preferred selectable marker for the Penicillium vectors of the invention and can be isolated from plasmid pPS51, described below.

B.(i) Construction of Plasmid pPS51

Figure 11:
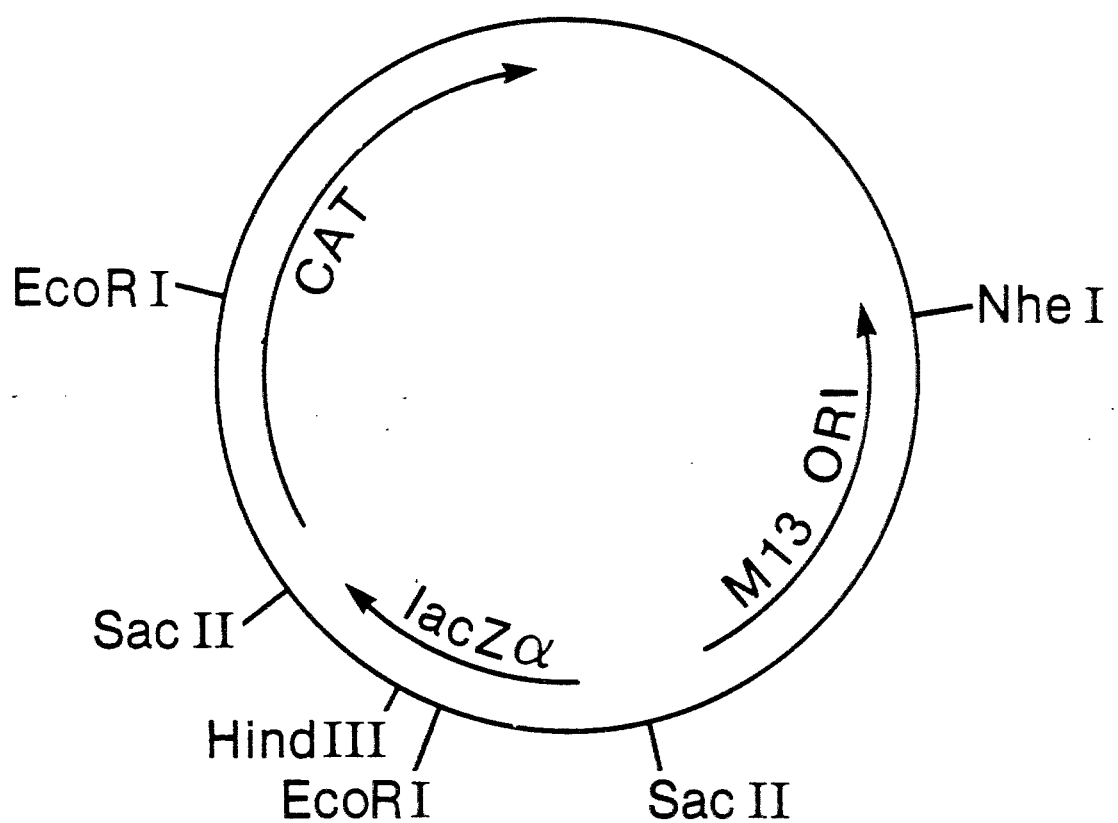
FIG. 11. Restriction site and function map of plasmid pMLC12.

About 15 μg of plasmid pMLC12 DNA (FIG. 11 and NRRL B-18097) were dissolved in 5 μl of 10× EcoRI buffer and 40 μl of water. About 5 μl (~50 units) of restriction enzyme EcoRI were added to the solution of DNA, and the resulting reaction was incubated at 37° C. for 3 minutes to produce a partial digestion. The reaction was terminated by extraction with buffered phenol, which was followed by extraction with chloroform. Plasmid pMLC12 contains two EcoRI restriction sites. The desired partial cleavage of the EcoRI site was to occur within the lacZα fragment and not within the CAT gene. This EcoRI digestion produced a mixture of plasmid pMLC12 DNA molecules: uncut; cut at the undesired location; cut at the desired location; and cut at both locations, producing fragments smaller than the full-length ~2.7 kb molecules. The EcoRI-digested plasmid pMLC12 DNA was precipitated, collected by centrifugation, dissolved in 50 μl of TE buffer, and loaded onto a 0.8% preparative agarose gel. The full length linear molecules (i.e., ~2.7 kb) were isolated.

The partially EcoRI-digested plasmid pMLC12 DNA was dissolved in 5 μl of 10× SalI buffer and 40 μl of water. About 5 μl (~50 units) of restriction enzyme SalI were added to the EcoRI-linearized plasmid pMLC12 DNA, and the resulting reaction was incubated at 37° C. for two hours. The unique SalI restriction site in plasmid pMLC12 is located 24 base pairs from the EcoRI site within the lacZα fragment of plasmid pMLC12. Thus, complete SalI digestion of the partially EcoRI-digested plasmid pMLC12 DNA produced four DNA fragments: one ~2.7 kb, the desired molecule; one ~24 bp in length; one ~0.6 kb; and one ~1.9 kb. The DNA molecules were size-fractionated on a 0.8% agarose gel. The nearly full-length, ~2.7 kb linear molecules were isolated.

Figure 12:
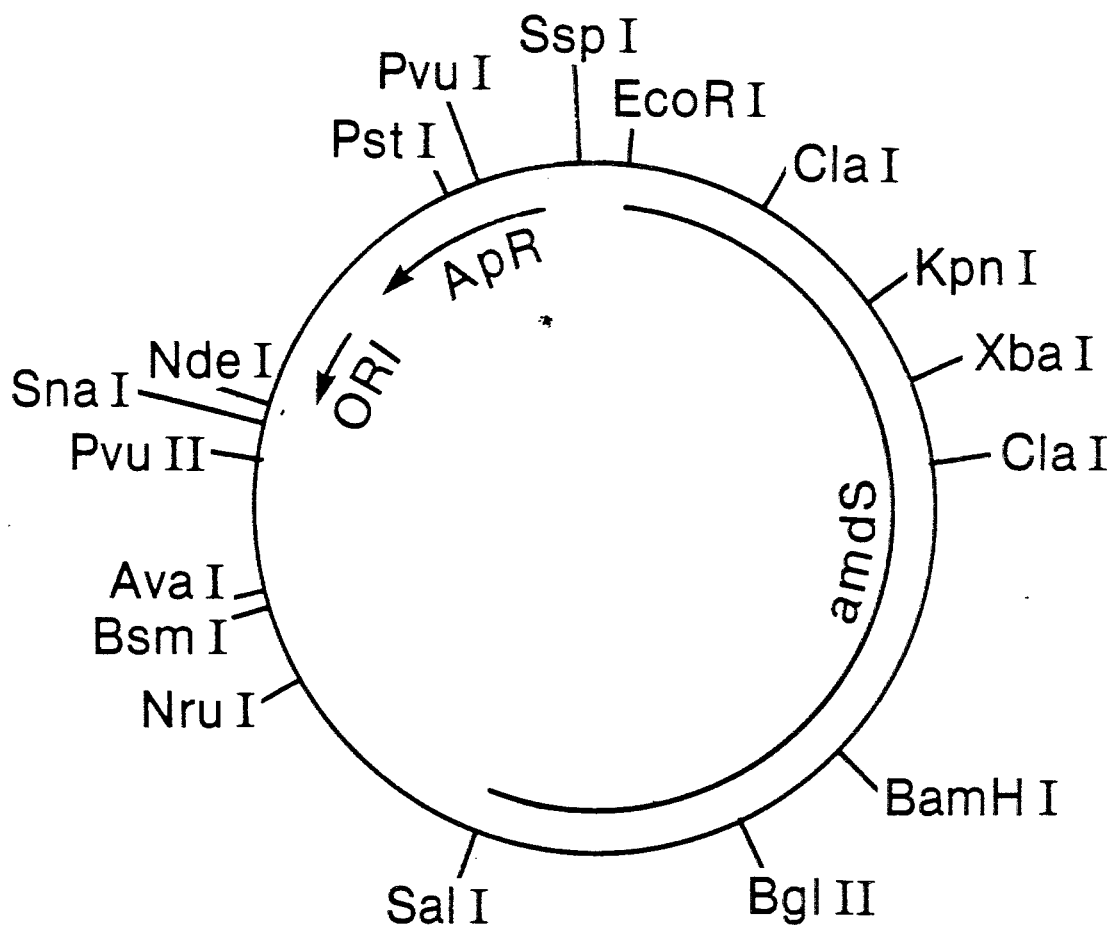
FIG. 12. Restriction site and function map of plasmid p3SR2.

The acetamidase gene of *Aspergillus nidulans* can be isolated on an ~5.0 kb EcoRI-SalI restriction fragment of plasmid p3SR2. About 10 μg of plasmid p3SR2 (FIG. 12 and NRRL B-18182) were dissolved in 5 μl of 10× EcoRI buffer and 40 μl of water. About 5 μl (~50 units) of restriction enzyme EcoRI were added to the solution of DNA, and the resulting reaction was incubated at 37° C. for two hours. The reaction was terminated by extraction with buffered phenol, which was followed by extraction with chloroform. The EcoRI-digested p3SR2 plasmid DNA was precipitated, collected by centrifugation, and resuspended in 5 μl of 10× SalI buffer and 40 μl of water. About 5 μl (~50 units) of restriction enzyme SalI were added to the solution of DNA, and the resulting reaction was incubated at 37° C. for two hours. The two DNA fragments generated in these digestions were size-fractionated on a 0.8% preparative agarose gel. One ~4.3 kb fragment comprised pBR322 DNA and the other ~5.0 kb fragment comprised the acetamidase (amdS) gene from *Aspergillus nidulans*. The ~5.0 kb EcoRI-SalI fragment was isolated. About 3 μg of the ~5.0 kb EcoRI-SalI fragment were recovered and suspended in 5 μl of water.

One μl of the EcoRI-SalI-digested plasmid pMLC12 DNA was added to about 4 μl of the ~5.0 kb EcoRI-SalI restriction fragment of plasmid p3SR2, together with 2 μl of 10× ligase buffer, 2 μl of T4 DNA ligase, and 11 μl of water. The resulting ligation reaction was incubated at 15° C. overnight. The ligated DNA constituted the desired plasmid pPS51 and other related ligation products.

Figure 13:
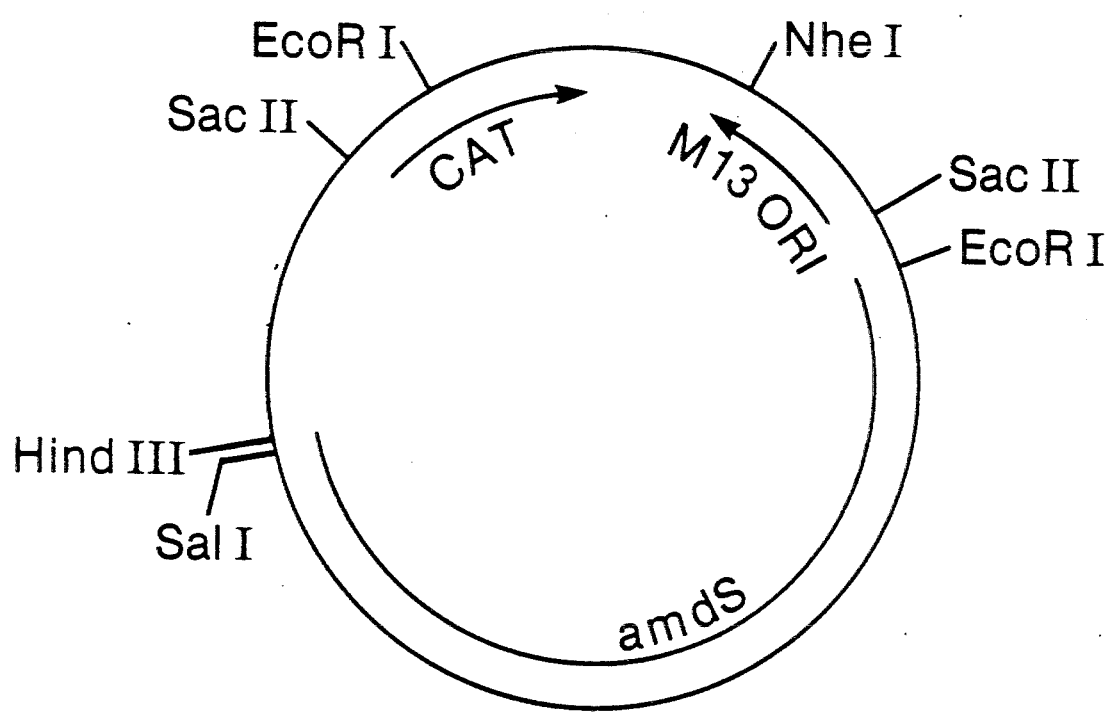
FIG. 13. Restriction site and function map of plasmid pPS51.

This ligation mixture was used to transform *E. coli* K12 C600 (ATCC 33524). Aliquots of the transformed cell mixture were plated on L-agar plates containing 25 μg/ml of chloramphenicol. The plates were incubated at 37° C. overnight. Colonies that contained a plasmid without an insert, such as *E. coli* K12 C600/pMLC12 were distinguished from colonies that contained a plasmid with an insert, such as *E. coli* K12 C600/pPS51, in substantial accordance with the method of Eckardt. A colony was identified that contained a plasmid with an insert. Plasmid DNA from this colony was screened by restriction analysis for the presence of the ~5.0 kb EcoRI-SalI restriction fragment containing the *Aspergillus nidulans* amdS gene and had the correct structure for the desired plasmid pPS51. A restriction site and function map of plasmid pPS51 is presented in FIG. 13 of the accompanying drawings.

B.(ii) Final Construction of Plasmids pPS65 and pPS66

The amdS gene can be isolated from plasmid pPS51 on an ~5.65 kb EcoRI restriction fragment. This ~5.65 kb fragment can be ligated to the large EcoRI restriction fragment of plasmid pPS64 to produce the desired plasmid pPS65. A restriction site and function map of plasmid pPS65 is presented in FIG. 5 of the accompanying drawings.

Because the amdS-containing, ~5.65 kb EcoRI restriction fragment of plasmid pPS51 could ligate in either orientation with the large EcoRI restriction fragment of plasmid pPS64, the above-described ligation also produces plasmid pPS66 of the invention. Plasmid pPS66 is identical to plasmid pPS65, except for the orientation of the amdS-containing, ~5.65 kb EcoRI restriction fragment.

A protocol for introducing plasmids into Pencillium is set forth in Example 8. Although all of plasmids pPS63, pPS64, pPS65, and pPS66 can be used to drive expression of DAOCS activity in Penicillium, only the latter two plasmids possess the amdS selectable marker.

EXAMPLE 6

Construction of Plasmids pPS67, pPS71, and pPS72

Those skilled in the art will recognize that the promoter of the Penicillium IPNS gene is merely illustrative of the invention, for any promoter can be used to drive expression of the DAOCS coding sequence. Plasmid pPS67 illustrates that the promoter of the amdS gene of *Aspergillus nidulans* can be used to drive expression of the DAOCS gene in Penicillium, Aspergillus, and any other organism in which the promoter functions.

Plasmid pPS67 is constructed by ligating together NdeI-digested plasmid pOW382, the ~745 bp, amdS promoter-containing restriction fragment of plasmid pPS51, and the following linker:

Figure 6:
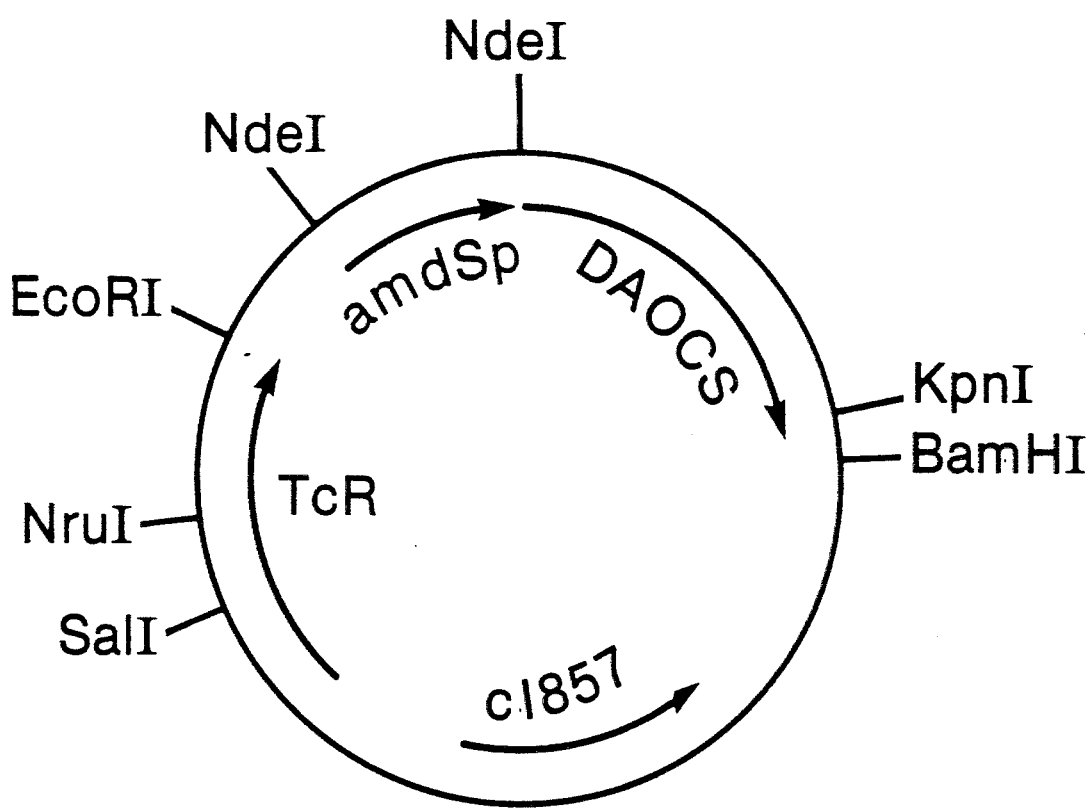
FIG. 6. Restriction site and function map of plasmid pPS67.

A restriction site and function map of plasmid pPS67 is presented in FIG. 6 of the accompanying drawings.

Figure 14:
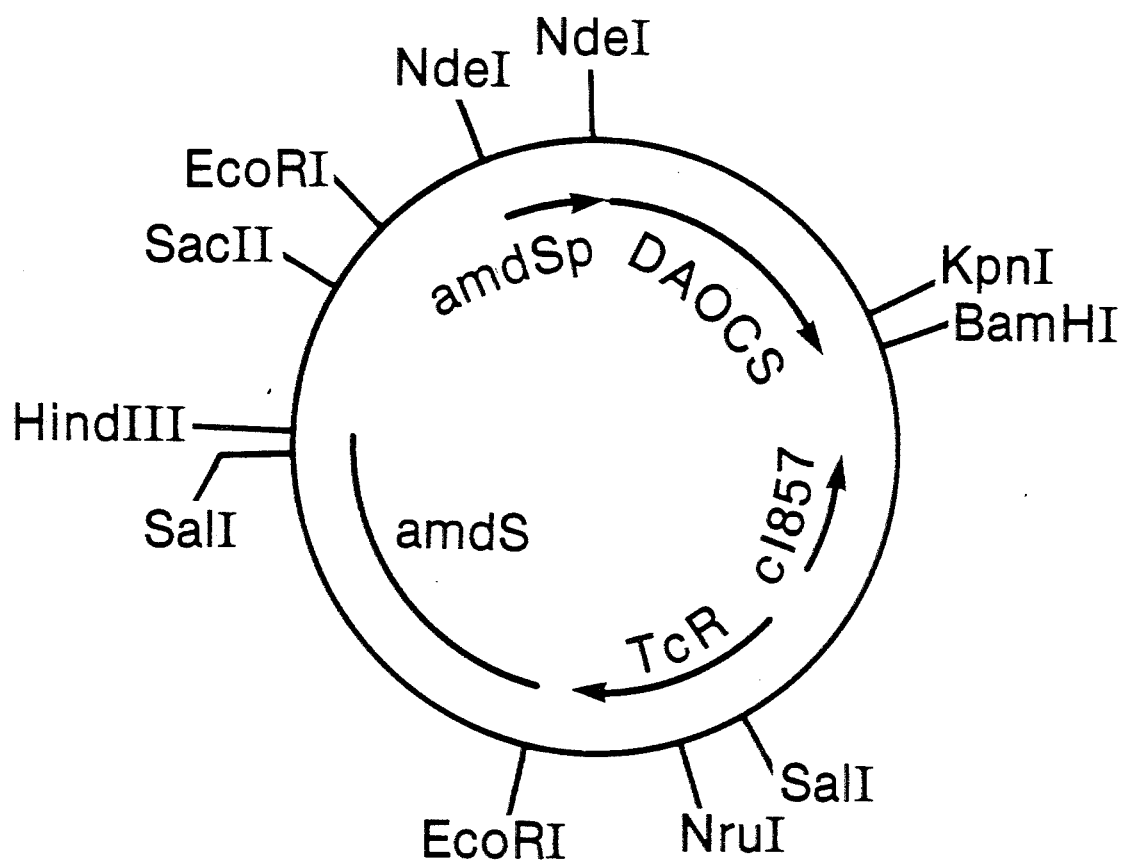
FIG. 14. Restriction site and function map of plasmid pPS71.

Plasmid pPS67 can be readily modified to include a selectable marker for use in Penicillium and Aspergillus host cells. Thus, plasmid pPS67 can be digested with restriction enzyme EcoRI and ligated with the ~5.65 kb, amdS-containing, EcoRI restriction fragment of plasmid pPS51 to yield plasmids pPS71 and pPS72. Plasmids pPS71 and pPS72 both contain the amdS gene and in fact differ only with respect to the orientation of the ~5.65 kb, amdS-containing, EcoRI restriction fragment. A restriction site and function map of plasmid pPS71 is presented in FIG. 14 of the accompanying drawings. A protocol for transforming Penicillium with vectors of the invention is set forth in Example 8.

EXAMPLE 7

Construction of Plasmid pPS69

Expression levels of recombinant proteins can be optimized by placing the coding sequence for the recombinant protein under the control of regulatory elements derived from the same species that will be used to produce the recombinant protein. These regulatory sequences include a promoter, located in the 5'-noncoding region of a gene, and terminator, located in the 3'-noncoding region of a gene. In plasmid pPS65, a preferred 1;AOCS expression vector for Penicillium, the coding sequence of the *Streptomyces clavuligerus* DAOCS gene is under the control of only the regulatory elements in the 5'-noncoding region of the Penicillium IPNS gene. Plasmid pPS69 illustrates a vector in which both the 5' and 3' regulatory elements are present in a Penicillium DAOCS expression vector of the invention.

A. Construction of Intermediate Plasmid pPS68

Figure 15:
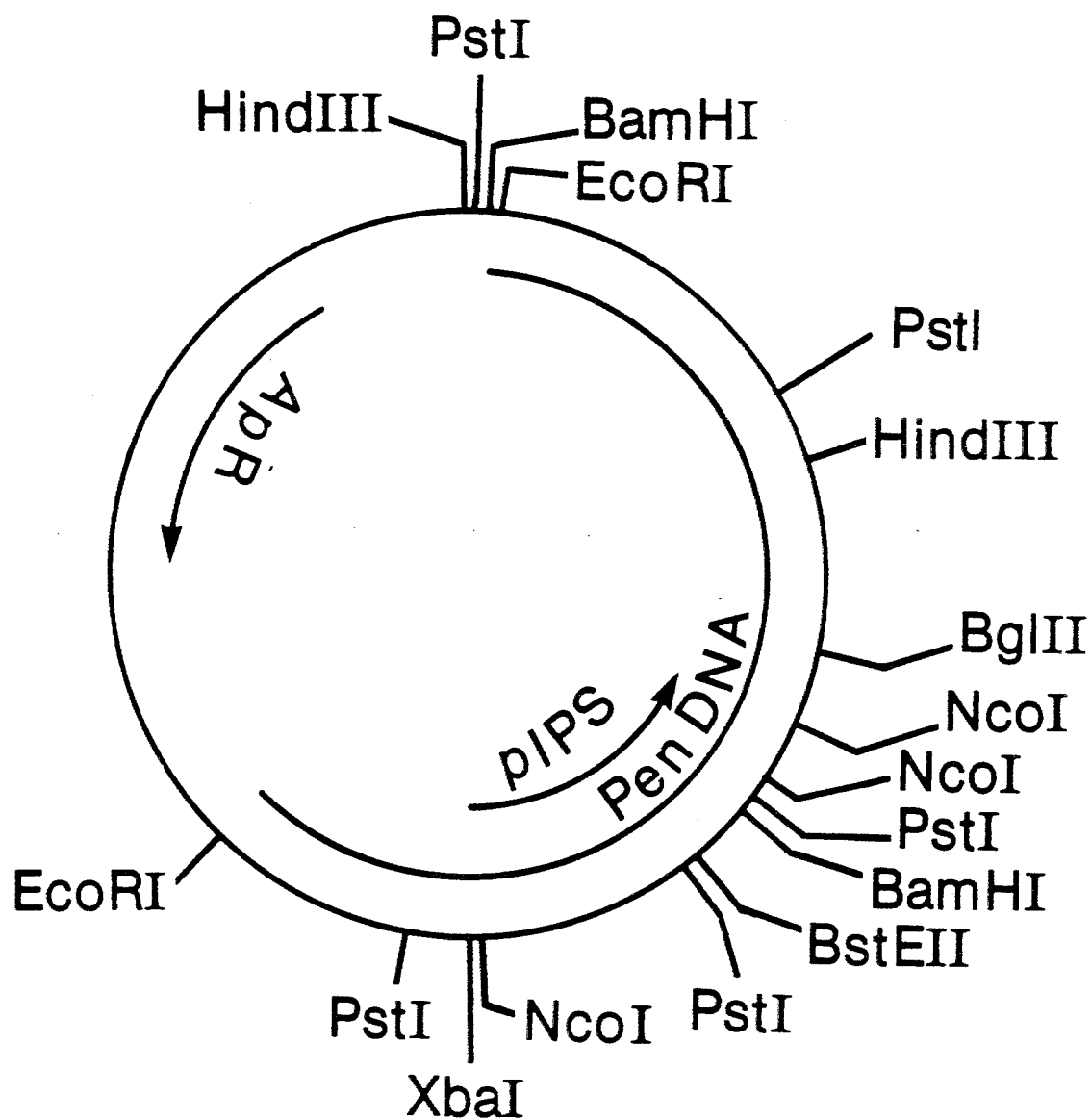
FIG. 15. Restriction site and function map of plasmid pLC2.

Plasmid pLC2 can be used as a source of the 3' regulatory region of the Penicillium IPNS gene. A lyophil of *E. coli* K12 JM109/pLC2 can be obtained from the American Type Culture Collection, Rockville, Md., under the accession number ATCC 53334. A restriction site and function map of plasmid pLC2 is presented in FIG. 15 of the accompanying drawings.

Plasmid pLC2 is digested with restriction enzyme PstI, and the ~1.1 kb, terminator-containing, restriction fragment is isolated, treated with Mung bean nuclease to remove the single-stranded 3' extensions, and prepared for ligation. Plasmid pPS64 is then digested with restriction enzyme KpnI, treated with Mung bean nuclease, and prepared for ligation.

Figure 16:
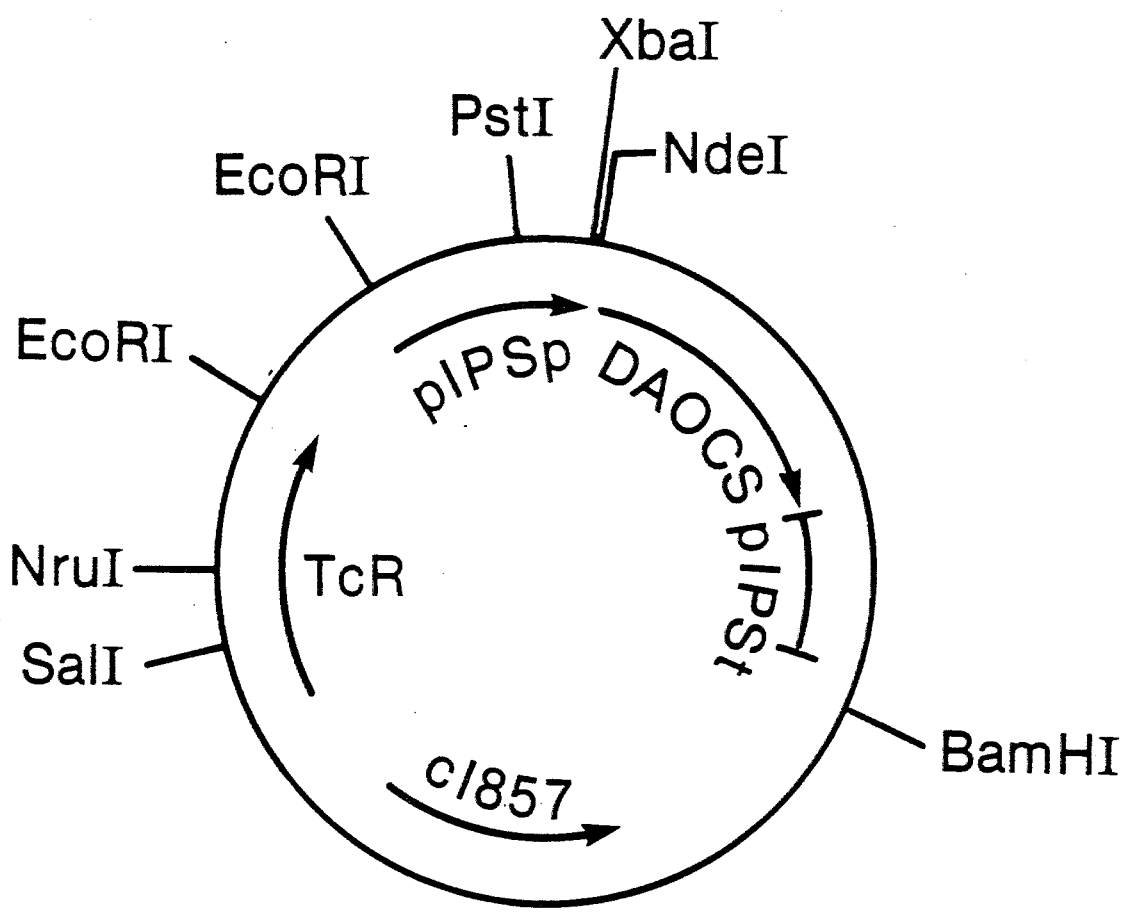
FIG. 16. Restriction site and function map of plasmid pPS68.

The KpnI-digested, nuclease treated plasmid pPS64 DNA is then ligated to the ~1.1 kb, 3' regulatory region-containing, nuclease-treated PstI restriction fragment of plasmid pLC2. The ligation produces plasmid pPS68. Because the ~1.1 kb fragment could ligate in one of two orientations, only one of which yields the desired plasmid pPS68, restriction enzyme analysis is used to identify the plasmid. A restriction site and function map of plasmid pPS68 is presented in FIG. 16 of the accompanying drawings.

Plasmid pPS68 can be used to drive expression of DAOCS in Penicillium host cells but does not contain a selectable marker. The addition of a selectable marker can be readily accomplished, however. For instance, plasmid pPS68 can be digested with restriction enzyme EcoRI and then ligated to the ~5.65 kb, amdS-containing, EcoRI restriction fragment of plasmid pPS51. This ligation produces plasmids pPS69 and pPS70, which differ only with respect to the orientation of the ~5.65 kb, amdS-containing, EcoRI restriction fragment. A restriction site and function map of plasmid pPS69 is presented in FIG. 7 of the accompanying drawings. A protocol for transforming Penicillium with vectors of the invention is set forth in Example 8.

EXAMPLE 8

Genetic Transformation of Penicillium

A. *Penicillium chrysohenum* Strains

A Penicillium strain for transformation is obtained from the American Type Culture Collection, Rockville, Md. 20852, under the accession number ATCC 9480. Other *Penicillium chrysogenum* strains or any commercial strains derived from ATCC 9480 by mutation, selection, or genetic breeding for the purpose of improved production of penicillin G or penicillin V are also suitable for use in preparing transformants with the vectors and plasmids of the present invention.

B. Preparation of Uniform Inoculum for Cell Culture

To transform *Penicillium chrysogenum* cells efficiently, it is necessary to remove the cell walls to form stable protoplasts. In the preparation of such protoplasts it is advantageous to begin with a uniform inoculum. Otherwise, preparation of cells in culture is not reproducible and time is lost by attempts to prepare *P. chrysogenum* protoplasts from unsuitable or inadequate amounts of cells.

An ampoule of vegetative ve cells (~10⁹ colony forming units in 1.0 ml of preservation menstrum: 5% lactose, 10% glycerol, and 0.1% Tween 80), either lyophilized or taken from liquid nitrogen storage and thawed at room temperature, are diluted in 1.0 ml of sterile saline. About 0.1 ml of this suspension is used to inoculate each of approximately 20 slants of sporulation medium: Lactose, 15.0 g/L; corn steep liquor, 2.5 g/L; peptone, 5.0 g/L; NaCl, 4.0 g/L; MgSO$_4$.7H$_2$O, 0.5 g/L; KH$_2$PO$_4$, 0.6 g/L; FeCl$_3$.6H$_2$O, 0.005 g/L; CuSO$_4$.5H$_2$O, 0.002 g/L; adjust to pH=7.0; agar, 30.0 g/L; and autoclave 20 minutes at 120 psi.

Each slant [15 cm×2.5 cm] contains 25 ml of solidified medium. Inoculum, spread evenly over the surface of the agar slant, is allowed to grow at 25° C. until a confluent lawn of mycelium is present and sporulated (1 week for most strains). The growth from 1 slant is suspended in 10 ml of sterile aqueous culture medium, and the suspension is transferred to 106 ml of aqueous culture medium. The flask containing the suspended cells is placed on a gyrotory shaker and incubated at 25° C. for 18 hours at 285 rpm with a 1 inch throw.

Aqueous culture medium was prepared as follows: 100 ml of solution A (Sucrose, 36 g/L; L-asparagine, 7.5 g/L; $KH_2PO_4$, 15 g/L; $K_2HPO_4$, 21 g/L; $NaSO_4$, 0.75 g/L; $MgSO_4.7H_2O$, 0.18 g/L; $CaCl_2$, 0.06 g/L; salts solution, 1 ml/L; and natural pH) are dispensed into a 500 ml shake flask; the flask is covered with a commercial closure and autoclaved at 121° C. for 20 minutes. Two ml of solution B (Glucose, 108 g/L) and 4 ml of solution C (Sucrose, 25 g/L; corn steep liquor (4% w/v nitrogen), 12.5 ml; ammonium acetate, 5.5 g/L; $CaCO_3$, 5 g/L; pH adjusted to 6.5 with KOH; and autoclaved at 121° C. for 20 minutes) are then added to solution A to prepare the aqueous culture medium.

C. Preparation of Penicillium protoplasts

Cells from a 24 hour culture are harvested by suction filtration (Whatman #1 paper in a Buchner funnel) and suspended in buffer (0.01 M Tris(hydroxymethyl)aminomethane hydrochloride; 0.01 M $MgSO_4$; 0.01 M dithiothreitol; 1.00 M KCl; and pH=7.0 with HCl). Sufficient buffer is added to obtain a final cell concentration of 1 g of cell mass per 50 ml of buffer. The cell suspension is placed on a gyrotory water bath shaker in a 250 ml shake flask and incubated at 29°–30° C. for 10 minutes at 140 rpm with a 1 inch throw. Dithiothreitol-treated cells are collected by centrifugation and then resuspended in 50 ml of enzyme solution (10 mg/ml Novozym, Novo industri A/B Bagsvaerd, Denmark; 0.01 M Tris(hydroxymethyl)aminomethane hydrochloride; 0.01 M $MgSO_4$; 0.01 M dithiothreitol; 1.00 M KCl; and pH=5.8 with HCl) in a 250 ml shake flask. This cell suspension is placed on a gyrotory water-bath shaker and incubated at 29°–30° C. for 15 minutes at 140 rpm with a 1 inch throw. Enzyme-treated cells are centrifuged at 1240× g for 6 min, and the resulting pellet is resuspended in buffer (0.01 M Tris(hydroxymethyl)aminomethane hydrochloride; 0.01 M $MgSO_4$; 1.00 M KCl; and pH=7.0 with HCl). The suspension is first centrifuged at 950× g for 6 minutes. The resulting pellet is resuspended in the same buffer, and the suspension is centrifuged at 700× g for 6 minutes. The resulting pellet is resuspended in 5 ml of the same buffer. This suspension contains primarily large protoplasts and osmotically fragile cells that retain some cell wall structure. Compared to the small protoplasts removed by the above procedure, the percentage of protoplasts able to regenerate cell walls and percentage of viable osmotically stable cells is higher for the large protoplasts and osmotically fragile cells in the final suspension. The suspension of cells is diluted with buffer to a concentration of ~2×10⁸ cells/ml.

D. Transformation Procedure

For each transforming plasmid, an ~0.1 ml suspension of osmotically fragile *Penicillium chrysogenum* cells (approximately 2×10⁷ cells) is supplemented with 10 μl of 50 mM $CaCl_2$, 25 μg of plasmid DNA in 5–15 μl of TE buffer, and 0.9 ml of a solution of freshly dissolved polyethylene glycol 4000 (Baker, 40% weight/volume in osmotically stabilized buffer). The mixture is vortexed, allowed to stand for 10 minutes at room temperature, centrifuged at 700× g for 2 minutes, and vortexed again. Two aliquots of 0.5 ml each are then spread on the surface of osmotically stabilized acetamide medium (1.7 g/L Yeast Nitrogen Base without amino acids and ammonium sulfate; 125 g/L sucrose, 0.738 g/L acetamide; 1.27 g/L $CaCl_2$; and 22 g/L Noble agar). To measure the total number of viable cells present in transformation mixtures, aliquots from the transformation mixture are plated on medium in which the acetamide is replaced with an equimolar amount of ammonium sulfate. Seven to ten days after transformation, transformant colonies of sufficient size to subculture are present on the acetamide medium. Abortive transformants are easily distinguished from stable transformants, because abortive transformants fail to grow upon subculture to fresh acetamide medium. Cells transformed with a plasmid containing the acetamidase gene form visible colonies in four to five days after transformation.

E. Analysis of Penicillium Transformants

Penicillium transformants that are transformed with vectors of the invention containing the amdS gene express an acetamidase activity (the amdS gene product) not detected in extracts of the untransformed recipient *P. chrysogenum* strain (e.g., ATCC 9480). This activity results in the ability of the transformed strains to grow using the ammonia released by acetamide hydrolysis when no other nitrogen sources are available. The Penicillium transformants of the invention also express DAOCS activity.

Stable transformants carry the transforming DNA in their high molecular weight DNA. Probes, e.g., the DAOCS coding sequence or fragments of Aspergillus DNA that contain the acetamidase gene, hybridize to the high molecular weight DNA from these transformants even after multiple passage on non-selective medium (ammonia as nitrogen source). The transforming phenotype (production of DAOCS and, if an amdS vector was used, ability to grow on acetamide as sole nitrogen source) is also maintained by the transformants after passage on non-selective medium.

DAOCS expression vectors that contain the acetamidase gene are particularly useful as vectors for inserting genes into *Penicillium chrysogenum*, because no special recipient strain, such as an auxotroph, need be constructed, owing to the natural inability of *P. chrysogenum* to grow on acetamide as sole nitrogen source. Transformation systems based on complementation of auxotrophic markers by a gene in the transforming plasmid do not share this advantage. Frequently, pleiotropic mutations are associated with the introduction of an auxotrophic marker into a *P. chrysogenum* strain highly developed for penicillin production. Such mutations usually result in lower penicillin production (MacDonald et al., 1963, J. Gen. Microbiol. 33: 365–374).

We claim:

1. A recombinant DNA molecule that encodes the DAOCS activity of *Streptomyces clavuligerus*.

2. The recombinant DNA molecule of claim 1 that encodes a protein of structure:

$H_2N$—Met Asp Thr Thr Val Pro Thr Phe Ser Leu Ala Glu
Leu Gln Gln Gly Leu His Gln Asp Glu Phe Arg Arg Cys
Leu Arg Asp Lys Gly Leu Phe Tyr Leu Thr Asp Cys Gly
Leu Thr Asp Thr Glu Leu Lys Ser Ala Lys Asp Ile Val
Ile Asp Phe Phe Glu His Gly Ser Glu Ala Glu Lys Arg
Ala Val Thr Ser Pro Val Pro Thr Met Arg Arg Gly Phe

-continued
Thr Gly Leu Glu Ser Glu Ser Thr Ala Gln Ile Thr Asn
Thr Gly Ser Tyr Ser Asp Tyr Ser Met Cys Tyr Ser Met
Gly Thr Ala Asp Asn Leu Phe Pro Ser Gly Asp Phe Glu
Arg Ile Trp Thr Gln Tyr Phe Asp Arg Gln Tyr Thr Ala
Ser Arg Ala Val Ala Arg Glu Val Leu Arg Ala Thr Gly
Thr Glu Pro Asp Gly Gly Val Glu Ala Phe Leu Asp Cys
Glu Pro Leu Leu Arg Phe Arg Tyr Phe Pro Gln Val Pro
Glu His Arg Ser Ala Glu Glu Gln Pro Leu Arg Met Ala
Pro His Tyr Asp Leu Ser Met Val Thr Leu Ile Gln Gln
Thr Pro Cys Ala Asn Gly Phe Val Ser Leu Gln Ala Glu
Val Gly Gly Ala Phe Thr Asp Leu Pro Tyr Arg Pro Asp
Ala Val Leu Val Phe Cys Gly Ala Ile Ala Thr Leu Val
Thr Gly Gly Gln Val Lys Ala Pro Arg His His Val Ala
Ala Pro Arg Arg Asp Gln Ile Ala Gly Ser Ser Arg Thr
Ser Ser Val Phe Phe Leu Arg Pro Asn Ala Asp Phe Thr
Phe Ser Val Pro Leu Ala Arg Glu Cys Gly Phe Asp Val
Ser Leu Asp Gly Glu Thr Ala Thr Phe Gln Asp Trp Ile
Gly Gly Asn Tyr Val Asn Ile Arg Arg Thr Ser Lys
Ala—COOH wherein Ala is an alanine residue, Arg is an arginine residue, Asn is an asparagine residue, Asp is an aspartic acid residue, —COOH is the carboxy terminus, Cys is a cysteine residue, Gln is a glutamine residue, Glu is a glutamic acid residue, Gly is a glycine residue, —H$_2$N is the amino terminus, His is a histidine residue, Ile is an isoleucine residue, Leu is a leucine residue, Lys is a lysine residue, Met is a methionine residue, Phe is a phenylalanine residue, Pro is a proline residue, Ser is a serine residue, Thr is a threonine residue, Trp is a tryptophan residue, Tyr is a tyrosine residue, and Val is a valine residue.

3. The recombinant DNA molecule of claim 2 that comprises the DNA sequence:

wherein A is deoxyadenyl, G is deoxyguanyl, C is deoxycytidyl, and T is thymidyl.

4. A recombinant DNA vector that comprises the DNA molecule of claim 2.

5. A recombinant DNA vector of claim 4 that further comprises a promoter operably linked to said DAOCS activity-encoding DNA.

6. The recombinant DNA expression vector of claim 5, wherein said promoter functions in *E. coli*.

7. The recombinant DNA expression vector of claim 6, wherein said promoter is the λpL promoter.

8. The recombinant DNA expression vector of claim 7 that is plasmid pOW382.

9. The recombinant DNA expression vector of claim 5, wherein said promoter functions in Aspergillus.

10. The recombinant DNA expression vector of claim 5, wherein said promoter functions in Penicillium.

11. The recombinant DNA expression vector of claim 10, wherein said promoter is the promoter of the *Penicillium chrysogenum* IPNS gene.

12. The recombinant DNA expression vector of claim 11 that is plasmid pPS63.

13. The recombinant DNA expression vector of claim 11 that is plasmid pPS64.

14. The recombinant DNA expression vector of claim 11 that is plasmid pPS65.

15. The recombinant DNA expression vector of claim 11 that is plasmid pPS66.

16. The recombinant DNA expression vector of claim 11 that is plasmid pPS68.

17. The recombinant DNA expression vector of claim 11 that is plasmid pPS69.

```
5'-ATG GAC ACG ACG GTG CCC ACC TTC AGC CTG GCC GAA CTC

CAG CAG GGC CTG CAC CAG GAC GAG TTC CGC AGG TGT CTG AGG GAC

AAG GGC CTC TTC TAT CTG ACG GAC TGC GGT CTG ACC GAC ACC GAG

CTG AAG TCG GCC AAG GAC ATC GTC ATC GAC TTC TTC GAG CAC GGC

AGC GAG GCG GAG AAG CGC GCC GTC ACC TCG CCC GTC CCC ACC ATG

CGC CGC GGC TTC ACC GGG CTG GAG TCG GAG AGC ACC GCC CAG ATC

ACC AAT ACC GGC AGC TAC TCC GAC TAC TCG ATG TGC TAC TCG ATG

GGC ACC GCG GAC AAC CTC TTC CCG TCC GGT GAC TTC GAG CGG ATC

TGG ACC CAG TAC TTC GAC CGC CAG TAC ACC GCC TCC CGC GCG GTC

GCC CGG GAG GTC CTG CGG GCG ACC GGG ACC GAG CCC GAC GGC GGG

GTC GAG GCC TTC CTC GAC TGC GAG CCG CTG CTG CGG TTC CGC TAC

TTC CCG CAG GTC CCC GAG CAC CGC AGC GCC GAG GAG CAG CCC CTG

CGG ATG GCG CCG CAC TAC GAC CTG TCG ATG GTC ACC CTC ATC CAG

CAG ACA CCC TGC GCC AAC GGC TTC GTC AGC CTC CAG GCC GAG GTC

GGC GGC GCG TTC ACG GAC CTG CCC TAC CGT CCG GAC GCC GTC CTC

GTC TTC TGC GGC GCC ATC GCG ACC CTG GTG ACC GGC GGC CAG GTC

AAG GCC CCC CGG CAC CAT GTC GCG GCC CCC CGC AGG GAC CAG ATA

GCG GGC AGC AGC CGC ACC TCC AGT GTG TTC TTC CTC CGT CCC AAC

GCG GAC TTC ACC TTC TCC GTC CCG CTG GCG CGC GAG TGC GGC TTC

GAT GTC AGC CTG GAC GGC GAG ACC GCC ACG TTC CAG GAT TGG ATC

GGG GGC AAC TAC GTG AAC ATC CGC CGC ACA TCC AAG GCA-3'
```

18. The recombinant DNA expression vector of claim 11 that is plasmid pPS70.

19. The recombinant DNA expression vector of claim 10, wherein said promoter is the promoter of the *Aspergillus nidulans* amdS gene.

20. The recombinant DNA expression vector of claim 19 that is plasmid pPS67.

21. The recombinant DNA expression vector of claim 19 that is plasmid pPS71.

22. The recombinant DNA expression vector of claim 19 that is plasmid pPS72.

23. The recombinant DNA expression vector of claim 5, wherein said promoter functions in Cephalosporium.

24. The recombinant DNA expression vector of claim 23, wherein said promoter is the promoter of the *Cephalosporium acremonium* DACS/DAOCS gene.

25. The recombinant DNA expression vector of claim 23, wherein said promoter is the promoter of the *Cephalosporium acremonium* IPNS gene.

26. The recombinant DNA expression vector of claim 5, wherein said promoter functions in Streptomyces.

27. The recombinant DNA expression vector of claim 4 that is pOW380.

28. The recombinant DNA expression vector of claim 4 that is pOW381.

29. A method for expressing DAOCS activity in a recombinant host cell, said method comprising:
  (1) transforming said host cell with a recombinant DNA expression vector that comprises:
    (a) a promoter that functions in said host cell; and
    (b) a DNA molecule of claim 2 operably linked to said promoter; and
  (2) culturing said host cell transformed in step (1) under conditions suitable for gene expression.

30. The method of claim 29, wherein said recombinant host cell is selected from the group consisting of *E. coli*, Cephalosporium, Streptomyces, Aspergillus, and Penicillium.

31. The method of claim 29, wherein said host cell is *E. coli*.

32. The method of claim 29, wherein said host cell is Streptomyces.

33. The method of claim 29, wherein said host cell is Penicillium.

34. The method of claim 29, wherein said host cell is Aspergillus.

35. The method of claim 29, wherein said host cell is Cephalosporium.

36. A recombinant host cell transformed with a recombinant DNA vector of claim 4.

37. The transformed host cell of claim 36 that is *E. coli* K12.

38. The transformed host cell of claim 37 that is *E. coli* K12 JA221/pOW380.

39. The transformed host cell of claim 36 that is *Penicillium*.

40. The transformed host cell of claim 39 that is *Penicillium chrysogenum*.

41. The transformed host cell of claim 39 that is *Penicillium chrysogenum*/pPS65.

42. The transformed host cell of claim 39 that is *Penicillium chrysogenum*/pPS66.

43. The transformed host cell of claim 39 that is *Penicillium chrysogenum*/pPS69.

44. The transformed host cell of claim 39 that is *Penicillium chrysogenum*/pPS70.

45. The transformed host cell of claim 39 that is *Penicillium chrysogenum*/pPS71.

46. The transformed host cell of claim 39 that is *Penicillium chrysogenum*/pPS72.

47. The transformed host cell of claim 36 that is Cephalosporium.

48. The transformed host cell of claim 36 that is Streptomyces.

49. The transformed host cell of claim 48 that is *Streptomyces clavuligerus*.

50. A recombinant DNA vector selected from the group consisting of mOW380 and mOW381.

* * * * *